(12) United States Patent
Chen

(10) Patent No.: US 11,939,576 B2
(45) Date of Patent: *Mar. 26, 2024

(54) TRANSGENIC MICROALGAE AND USE THEREOF AS A FEED FOR DELIVERY OF INTERFERING RNA MOLECULES

(71) Applicant: TRANSALGAE ISRAEL LTD., Rehovot (IL)

(72) Inventor: Ofra Chen, Rehovot (IL)

(73) Assignee: TRANSALGAE ISRAEL LTD., Rehovot (IL)

( * ) Notice: Subject to any disclaimer, the term of this patent is extended or adjusted under 35 U.S.C. 154(b) by 534 days.

This patent is subject to a terminal disclaimer.

(21) Appl. No.: 17/003,254

(22) Filed: Aug. 26, 2020

(65) Prior Publication Data

US 2021/0032625 A1 Feb. 4, 2021

Related U.S. Application Data

(63) Continuation of application No. 15/741,898, filed as application No. PCT/IL2016/050760 on Jul. 14, 2016, now Pat. No. 10,781,447.

(60) Provisional application No. 62/192,082, filed on Jul. 14, 2015.

(51) Int. Cl.

| | |
|---|---|
| C12N 15/113 | (2010.01) |
| A01N 65/00 | (2009.01) |
| A01N 65/03 | (2009.01) |
| A23K 10/16 | (2016.01) |
| A23K 20/00 | (2016.01) |
| A23K 20/153 | (2016.01) |
| A23K 50/10 | (2016.01) |
| A23K 50/80 | (2016.01) |
| A23L 17/60 | (2016.01) |
| A61K 31/713 | (2006.01) |
| A61K 36/02 | (2006.01) |
| C12N 1/12 | (2006.01) |
| C12N 15/11 | (2006.01) |
| C12N 15/82 | (2006.01) |

(52) U.S. Cl.
CPC ............ *C12N 15/113* (2013.01); *A01N 65/00* (2013.01); *A01N 65/03* (2013.01); *A23K 10/16* (2016.05); *A23K 20/00* (2016.05); *A23K 20/153* (2016.05); *A23K 50/10* (2016.05); *A23K 50/80* (2016.05); *A23L 17/60* (2016.08); *A61K 31/713* (2013.01); *A61K 36/02* (2013.01); *C12N 1/12* (2013.01); *C12N 15/111* (2013.01); *C12N 15/1131* (2013.01); *C12N 15/8286* (2013.01); *C12N 2310/14* (2013.01); *C12N 2320/32* (2013.01); *Y02A 40/146* (2018.01)

(58) Field of Classification Search
CPC .... C12N 15/113; C12N 15/8286; C12N 1/12; C12N 2310/14; A61N 65/03

USPC ...... 424/9.1; 435/6.1, 91.1, 91.31, 455, 458; 514/44 A, 44 R; 536/23.1, 24.5
See application file for complete search history.

(56) References Cited

U.S. PATENT DOCUMENTS

| | | | |
|---|---|---|---|
| 7,410,637 | B2 | 8/2008 | Sayre |
| 8,404,832 | B2 | 3/2013 | Natt |
| 8,445,456 | B2 | 5/2013 | Tsai |
| 8,524,679 | B2 | 9/2013 | Pachuk |
| 8,633,028 | B2 | 1/2014 | Gross |
| 10,781,447 | B2 * | 9/2020 | Chen ..................... A23K 20/00 |
| 2008/0107652 | A1 | 5/2008 | Durvasula |
| 2008/0194504 | A1 | 8/2008 | Kyle |
| 2011/0081706 | A1 | 4/2011 | Schlesinger |
| 2013/0315883 | A1 | 11/2013 | Sayre |
| 2014/0271559 | A1 | 9/2014 | Baum |
| 2015/0096078 | A1 | 4/2015 | Dawson |
| 2018/0355325 | A1 * | 12/2018 | Dawson ............ C12N 15/8203 |
| 2019/0071690 | A1 * | 3/2019 | McGonigle ........ C12N 15/8286 |

FOREIGN PATENT DOCUMENTS

| | | |
|---|---|---|
| CN | 1860220 A | 11/2006 |
| CN | 102550864 A | 7/2012 |
| CN | 103269579 A | 8/2013 |
| CN | 104754954 A | 7/2015 |
| JP | 2007-530414 A | 11/2007 |
| WO | 97039106 A1 | 10/1997 |
| WO | 2005005613 A2 | 1/2005 |
| WO | 2005079236 A2 | 9/2005 |

(Continued)

OTHER PUBLICATIONS

Williams et al (An Overview of Diatom Classification with Some Prospects for the Future, in The Diatom World, Cellular Origin, Life in Extreme Habitats and Astrobiology, vol. 19, pp. 47-91 (J. Seckbach and J.P. Kociolek (eds.) (2011) (Year: 2011).*

(Continued)

*Primary Examiner* — Jane J Zara
(74) *Attorney, Agent, or Firm* — Rodney J. Fuller; BOOTH UDALL FULLER, PLC

(57) ABSTRACT

The present invention provides non-propagating transgenic microalgae expressing at least one heterologous RNAi molecule. The RNAi-expressing non-propagating transgenic microalgae are used for oral delivery of the RNAi molecule to a target organism in its intact and functional form. The heterologous RNAi molecule, present within the microalgae, is characterized by being biologically active, exerting at least one specific effect on the organism consuming the microalgae or on a pathogen of said organism. In particular, the non-propagating transgenic microalgae are used as agents for biological control of animal and plant pests.

5 Claims, 12 Drawing Sheets

Figure 1:
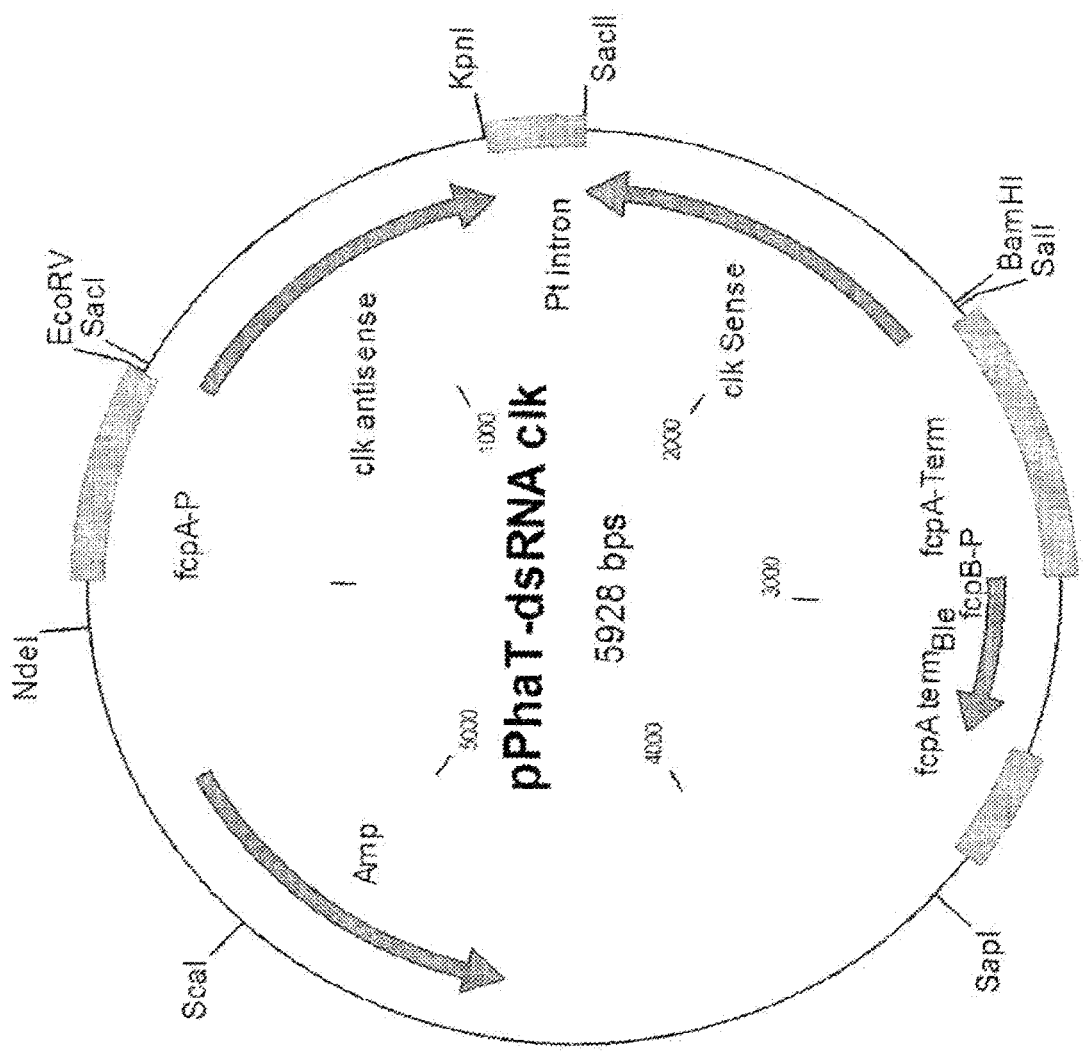

Specification includes a Sequence Listing.

(56) References Cited

FOREIGN PATENT DOCUMENTS

| WO | 2012023960 A2 | 2/2012 | |
|---|---|---|---|
| WO | 2012054919 A2 | 4/2012 | |
| WO | WO-2012054919 A2 * | 4/2012 | ............ A23K 20/153 |

OTHER PUBLICATIONS

Kumar et al (Malaria World Journal, vol. 4, No. 6, pp. 1-7 (2013)) (Year: 2013).*
Lerner et al (Nat. Commun., vol. 6: 7056, pp. 1-27 (May 8, 2015)) (Year: 2015).*
Luo et al (genes & Development, vol. 26, pp. 2536-2549 (2012)) (Year: 2012).*
Avila-Roman et al., (2014) Preventive effect of the microalga *Chlamydomonas debaryana* on the acute phase of experimental colitis in rats. Br J Nutr 112(7): 1055-1064.
Sugiyama et al., (2013) Dry Powdered Unicellular Alga *Parachlorella kessleri* Strain KNK-A001 as a Useful Feed for Pacific Oyster *Crassostrea gigas* Spat and Zooplankton Rotifer *Brachionus plicatilis*. Aquaculture Science 61(4): 389-394. Abstract.
Schistocerca gregaria clock protein mRNA, partial cds. GenBank: HQ428033.2. Tobback,J. et al., Jul. 12, 2012; 1 page.
Yamasato Kazuhide (1980) Preservation of Microorganisms by Freezing and Drying. The Journal of Japanese Society for Cryobiology and Cryotechnology 26: 11-14. With machine translation of introduction.
Cogoni and Macino (2000) Post-transcriptional gene silencing across kingdoms. Current Opinion in Genetics & Development 10(6): 638-643.
Dauwalder et al., (2002) The *Drosophila* takeout gene is regulated by the somatic sex-determination pathway and affects male courtship behavior. Genes & Development 16(22): 2879-2892.
Escobedo-Bonilla (2011) Application of RNA Interference (RNAi) against Viral Infections in Shrimp: A Review. J Antivir Antiretrovir S9: 1-12.
Guo and Kemphues (1995) par-1, a gene required for establishing polarity in C. elegans embryos, encodes a putative Ser/Thr kinase that is asymmetrically distributed. Cell 81(4): 611-620.
Katoch et al., (2013) RNAi for insect control: current perspective and future challenges. Applied Biochemistry and Biotechnology 171(4): 847-873.
Kennerdell and Carthew (2000) Heritable gene silencing in *Drosophila* using double-stranded RNA. Nature Biotechnology 18(8): 896-898.
Klink et al., (2009) A correlation between host-mediated expression of parasite genes as tandem inverted repeats and abrogation of development of female Heterodera glycines cyst formation during infection of Glycine max. Planta 230(1): 53-71.
Kumar et al., (2013) Development of an RNAi based microalgal larvicide to control mosquitoes. MalariaWorld Journal 4(6): 1-7.
Livak and Schmittgen (2001) Analysis of relative gene expression data using real-time quantitative PCR and the 2-$\Delta\Delta$CT method. Methods 25(4): 402-408.
Price and Gatehouse (2008) RNAi-mediated crop protection against insects. Trends in Biotechnology 26(7): 393-400.
Stein and Cheng (1993) Antisense oligonucleotides as therapeutic agents—is the bullet really magical? Science 261(5124): 1004-1012.
Thompson et al., (1994) Clustal W: improving the sensitivity of progressive multiple sequence alignment through sequence weighting, position-specific gap penalties and weight matrix choice. Nucleic Acids Research 22(22): 4673-4680.
Tobback et al., (2011) The circadian clock genes affect reproductive capacity in the desert locust *Schistocerca gregaria*. Insect Biochemistry and Molecular Biology 41(5): 313-321.
Tobback et al., (2012) RNA interference mortality points to noncircadian functions for the clock gene in the desert locust *Schistocerca gregaria*. Insect Molecular Biology 21(3): 369-381.
Tröße et al., (2014) RNA interference mediated knockdown of the KDEL receptor and COPB2 inhibits digestion and reproduction in the parasitic copepod *Lepeophtheirus salmonis*. Comp Biochem Physiol B Biochem Mol Biol 170: 1-9.
Wianny and Zernicka-Goetz (2000) Specific interference with gene function by double-stranded RNA in early mouse development. Nature Cell Biology 2(2): 70-75.
Williams DM and Kociolek JP (2011) An Overview of Diatom Classification with Some Prospects for the Future. In: Seckbach J, Kociolek P (eds) The Diatom World. Cellular Origin, Life in Extreme Habitats and Astrobiology, vol. 19. Springer, Dordrecht; pp. 47-91.
Yadav et al., (2006) Host-generated double stranded RNA induces RNAi in plant-parasitic nematodes and protects the host from infection. Molecular and Biochemical Parasitology 148(2): 219-222.

* cited by examiner

SEQUENCE LISTING

```
<160> NUMBER OF SEQ ID NOS: 37

<210> SEQ ID NO 1
<211> LENGTH: 820
<212> TYPE: DNA
<213> ORGANISM: Schistocerca gregaria
<220> FEATURE:
<221> NAME/KEY: misc_feature
<222> LOCATION: (781)..(781)
<223> OTHER INFORMATION: n is a, c, g, t or u

<400> SEQUENCE: 1
ctatgattat taccatgtgg atgatcttga gaaagttgtc acgtgccatg aagctttgat      60
gcagaaggga gaaggtactt cttgccatta tcgttttctg accaaagggc agcagtggat     120
atggttacaa actaggttct acataactta ccatcaatgg aactcaaagc cagagttcat     180
tgtatgcaca cacagagttg tcagttacat ggatgtaatg aagcaaatga gaaaggaccc     240
tgaagaaggt gaacgaagcc aagacagtga gatgggtgca tgggagtctt ctgataaaca     300
agtgggtact acatcacaag gtagcatctc ttctagtgcc tggacgtctc ggtcctcagg     360
aaaagtatct agagcagaga caaatcgcc agtgacacag aagcagcatc agtctggatg     420
tactacgaac acagttcctt ctgcagctac tactccaggt tctgctacac ctagtcctgg     480
atctgcatgt gattctgctg tgggtgttgc agcaaccagc tcctctgcac aggcaacatc     540
atcaaggaat tcacaactta gcacgcgacg gtcgaagtca gtcagcagca aattacagat     600
```

| | |
|---|---|
| gcctgtaact ccaccagctc aacagcagcg gcaacagcag cagcagcagc agcagcagca | 660 |
| acaacaacca caacaacagc aacagcagca gcaacaagaa cagtcatcat caaatgcgat | 720 |
| accaacctca acgtcccaag tttcactacc agtggcagct ccattcttag aagcccagca | 780 |
| ncaatatgtt acagccatac ctgtccagcc agtattggct | 820 |

```
<210> SEQ ID NO 2
<211> LENGTH: 464
<212> TYPE: DNA
<213> ORGANISM: Artificial Sequence
<220> FEATURE:
<223> OTHER INFORMATION: Synthetic polynucleotide

<400> SEQUENCE: 2
```

| | |
|---|---|
| ggatccaagg gcagcagtgg atatggttac aaactaggtt ctacataact taccatcaat | 60 |
| ggaactcaaa gccagagttc attgtatgca cacacagagt tgtcagttac atggatgtaa | 120 |
| tgaagcaaat gagaaaggac cctgaagaag gtgaacgaag ccaagacagt gagatgggtg | 180 |
| catgggagtc ttctgataaa caagtgggta ctacatcaca aggtagcatc tcttctagtg | 240 |
| cctggacgtc tcggtcctca ggaaaagtat ctagagcaga gacaaaatcg ccagtgacac | 300 |
| agaagcagca tcagtctgga tgtactacga acacagttcc ttctgcagct actactccag | 360 |
| gttctgctac acctagtcct ggatctgcat gtgattctgc tgtgggtgtt gcagcaacca | 420 |
| gctcctctgc acaggcaaca tcatcaagga attcacaacc gcgg | 464 |

```
<210> SEQ ID NO 3
<211> LENGTH: 464
<212> TYPE: DNA
<213> ORGANISM: Artificial Sequence
<220> FEATURE:
<223> OTHER INFORMATION: Synthetic polynucleotide

<400> SEQUENCE: 3
```

| | |
|---|---|
| ggtaccttgt gaattccttg atgatgttgc ctgtgcagag gagctggttg ctgcaacacc | 60 |
| cacagcagaa tcacatgcag atccaggact aggtgtagca gaacctggag tagtagctgc | 120 |
| agaaggaact gtgttcgtag tacatccaga ctgatgctgc ttctgtgtca ctggcgattt | 180 |
| tgtctctgct ctagatactt ttcctgagga ccgagacgtc caggcactag aagagatgct | 240 |
| accttgtgat gtagtaccca cttgtttatc agaagactcc catgcaccca tctcactgtc | 300 |
| ttggcttcgt tcaccttctt cagggtcctt tctcatttgc ttcattacat ccatgtaact | 360 |
| gacaactctg tgtgtgcata caatgaactc tggctttgag ttccattgat ggtaagttat | 420 |
| gtagaaccta gtttgtaacc atatccactg ctgcccttga gctc | 464 |

```
<210> SEQ ID NO 4
<211> LENGTH: 552
<212> TYPE: DNA
<213> ORGANISM: Artificial Sequence
<220> FEATURE:
<223> OTHER INFORMATION: Synthetic polynucleotide

<400> SEQUENCE: 4
```

| | |
|---|---|
| ggatccatgg tgagcaaggg cgaggagctg ttcaccgggg tggtgcccat cctggtcgag | 60 |
| ctggacggcg acgtaaacgg ccacaagttc agcgtgtccg gcgagggcga gggcgatgcc | 120 |
| acctacggca agctgaccct gaagttcatc tgcaccaccg gcaagctgcc cgtgccctgg | 180 |
| cccaccctcg tgaccaccct gacctacggc gtgcagtgct tcagccgcta ccccgaccac | 240 |
| atgaagcagc acgacttctt caagtccgcc atgcccgaag gctacgtcca ggagcgcacc | 300 |

-continued

```
atcttcttca aggacgacgg caactacaag acccgcgccg aggtgaagtt cgagggcgac      360
accctggtga accgcatcga gctgaagggc atcgacttca aggaggacgg caacatcctg      420
gggcacaagc tggagtacaa ctacaacagc cacaacgtct atatcatggc cgacaagcag      480
aagaacggca tcaaggtgaa cttcaagatc cgccacaaca tcgaggacgg cagcgtgcag      540
ctcgccccgc gg                                                         552
```

<210> SEQ ID NO 5
<211> LENGTH: 552
<212> TYPE: DNA
<213> ORGANISM: Artificial Sequence
<220> FEATURE:
<223> OTHER INFORMATION: Synthetic polynucleotide

<400> SEQUENCE: 5

```
ggtaccggcg agctgcacgc tgccgtcctc gatgttgtgg cggatcttga agttcacctt      60
gatgccgttc ttctgcttgt cggccatgat atagacgttg tggctgttgt agttgtactc      120
cagcttgtgc cccaggatgt tgccgtcctc cttgaagtcg atgcccttca gctcgatgcg      180
gttcaccagg gtgtcgccct cgaacttcac ctcggcgcgg tcttgtagt tgccgtcgtc       240 cttgaagaag atggtgcgct cctggacgta gccttcgggc atggcggact tgaagaagtc      300
gtgctgcttc atgtggtcgg ggtagcggct gaagcactgc acgccgtagg tcagggtggt      360
cacgagggtg ggccagggca cggcagcttg ccggtggtg cagatgaact tcagggtcag       420
cttgccgtag gtggcatcgc cctcgccctc gccggacacg ctgaacttgt ggccgtttac      480
gtcgccgtcc agctcgacca ggatgggcac caccccggtg aacagctcct cgcccttgct      540
caccatgagc tc                                                         552
```

<210> SEQ ID NO 6
<211> LENGTH: 205
<212> TYPE: DNA
<213> ORGANISM: Artificial Sequence
<220> FEATURE:
<223> OTHER INFORMATION: Synthetic polynucleotide

<400> SEQUENCE: 6

```
ccgcggggt acgtattgca ctttagccgc aacgtacctt gtgtgatcgt tttatgccgg       60
cattctgaca catgttttct tctatacgta gggtaagaat ggttccttac aattttaaaa     120
acatgttcat tttgtttccg acggcacact cgtggacatt ctccctcaca aaacaagaat     180 cttttttgtgc tctgcgtagg gtacc                                          205
```

<210> SEQ ID NO 7
<211> LENGTH: 21
<212> TYPE: DNA
<213> ORGANISM: Artificial Sequence
<220> FEATURE:
<223> OTHER INFORMATION: Synthetic polynucleotide (primer)

<400> SEQUENCE: 7

```
accggagtca agagcacaca c                                                21
```

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide (primer)

```
<400> SEQUENCE: 8
cggaatgcgc gtataccagt                                              20

<210> SEQ ID NO 9
<211> LENGTH: 18
<212> TYPE: DNA
<213> ORGANISM: Artificial Sequence
<220> FEATURE:
<223> OTHER INFORMATION: Synthetic polynucleotide (primer)

<400> SEQUENCE: 9
gcagctcgcc ggtaccta                                                18

<210> SEQ ID NO 10
<211> LENGTH: 19
<212> TYPE: DNA
<213> ORGANISM: Artificial Sequence
<220> FEATURE:
<223> OTHER INFORMATION: Synthetic polynucleotide (primer)

<400> SEQUENCE: 10
ttgtttccga cggcacact                                               19

<210> SEQ ID NO 11
<211> LENGTH: 22
<212> TYPE: DNA
<213> ORGANISM: Artificial Sequence
<220> FEATURE:
<223> OTHER INFORMATION: Synthetic polynucleotide (primer)

<400> SEQUENCE: 11
ccgtcatgca gaaaaagacc at                                           22

<210> SEQ ID NO 12
<211> LENGTH: 21
<212> TYPE: DNA
<213> ORGANISM: Artificial Sequence
<220> FEATURE:
<223> OTHER INFORMATION: Synthetic polynucleotide (primer)

<400> SEQUENCE: 12
ctgcgtaggt accctgcttg a                                            21

<210> SEQ ID NO 13
<211> LENGTH: 23
<212> TYPE: DNA
<213> ORGANISM: Artificial Sequence
<220> FEATURE:
<223> OTHER INFORMATION: Synthetic polynucleotide (primer)

<400> SEQUENCE: 13
ggacattctc cctcacaaaa caa                                          23

<210> SEQ ID NO 14
<211> LENGTH: 22
<212> TYPE: DNA
<213> ORGANISM: Artificial Sequence
<220> FEATURE:
<223> OTHER INFORMATION: Synthetic polynucleotide (primer)

<400> SEQUENCE: 14
caaatgcgat accaacctca ac                                           22

<210> SEQ ID NO 15
<211> LENGTH: 20
```

```
<212> TYPE: DNA
<213> ORGANISM: Artificial Sequence
<220> FEATURE:
<223> OTHER INFORMATION: Synthetic polynucleotide (primer)

<400> SEQUENCE: 15
gtctgatgac aacagtgcat                                              20

<210> SEQ ID NO 16
<211> LENGTH: 21
<212> TYPE: DNA
<213> ORGANISM: Artificial Sequence
<220> FEATURE:
<223> OTHER INFORMATION: Synthetic polynucleotide (primer)

<400> SEQUENCE: 16
gtccatcacg ccacaacttt c                                            21

<210> SEQ ID NO 17
<211> LENGTH: 24
<212> TYPE: DNA
<213> ORGANISM: Artificial Sequence
<220> FEATURE:
<223> OTHER INFORMATION: Synthetic polynucleotide (primer)

<400> SEQUENCE: 17
aattaccatt ggtaacgagc gatt                                         24

<210> SEQ ID NO 18
<211> LENGTH: 21
<212> TYPE: DNA
<213> ORGANISM: Artificial Sequence
<220> FEATURE:
<223> OTHER INFORMATION: Synthetic polynucleotide (primer)

<400> SEQUENCE: 18
tgcttccata cccaggaatg a                                            21

<210> SEQ ID NO 19
<211> LENGTH: 23
<212> TYPE: DNA
<213> ORGANISM: Artificial Sequence
<220> FEATURE:
<223> OTHER INFORMATION: Synthetic polynucleotide (primer)

<400> SEQUENCE: 19
ttggaattgg agttggaaca tgt                                          23

<210> SEQ ID NO 20
<211> LENGTH: 24
<212> TYPE: DNA
<213> ORGANISM: Artificial Sequence
<220> FEATURE:
<223> OTHER INFORMATION: Synthetic polynucleotide (primer)

<400> SEQUENCE: 20
agtctaccaa tggatggttt gaca                                         24

<210> SEQ ID NO 21
<211> LENGTH: 19
<212> TYPE: DNA
<213> ORGANISM: Artificial Sequence
<220> FEATURE:
<223> OTHER INFORMATION: Synthetic polynucleotide (primer)

<400> SEQUENCE: 21
```
accagatcgg agccagctt                                          19

<210> SEQ ID NO 22
<211> LENGTH: 24
<212> TYPE: DNA
<213> ORGANISM: Artificial Sequence
<220> FEATURE:
<223> OTHER INFORMATION: Synthetic polynucleotide (primer)

<400> SEQUENCE: 22
cttctggatg ttgtcgttgt agtt                                    24

<210> SEQ ID NO 23
<211> LENGTH: 22
<212> TYPE: DNA
<213> ORGANISM: Artificial Sequence
<220> FEATURE:
<223> OTHER INFORMATION: Synthetic polynucleotide (primer)

<400> SEQUENCE: 23
ccatgaagct ttgatgcaga ag                                      22

<210> SEQ ID NO 24
<211> LENGTH: 22
<212> TYPE: DNA
<213> ORGANISM: Artificial Sequence
<220> FEATURE:
<223> OTHER INFORMATION: Synthetic polynucleotide (primer)

<400> SEQUENCE: 24
ctggctttga gttccattga tg                                      22

<210> SEQ ID NO 25
<211> LENGTH: 26
<212> TYPE: DNA
<213> ORGANISM: Artificial Sequence
<220> FEATURE:
<223> OTHER INFORMATION: Synthetic polynucleotide (primer)

<400> SEQUENCE: 25
gggatccatg gtgagcaagg gcgagg                                  26

<210> SEQ ID NO 26
<211> LENGTH: 25
<212> TYPE: DNA
<213> ORGANISM: Artificial Sequence
<220> FEATURE:
<223> OTHER INFORMATION: Synthetic polynucleotide (primer)

<400> SEQUENCE: 26
gccgcggggc gagctgcacg ctgcc                                   25

<210> SEQ ID NO 27
<211> LENGTH: 26
<212> TYPE: DNA
<213> ORGANISM: Artificial Sequence
<220> FEATURE:
<223> OTHER INFORMATION: Synthetic polynucleotide (primer)

<400> SEQUENCE: 27
ggagctcatg gtgagcaagg gcgagg                                  26

<210> SEQ ID NO 28
<211> LENGTH: 25
<212> TYPE: DNA
<213> ORGANISM: Artificial Sequence

```
<220> FEATURE:
<223> OTHER INFORMATION: Synthetic polynucleotide (primer)

<400> SEQUENCE: 28
gggtaccggc gagctgcacg ctgcc                                            25

<210> SEQ ID NO 29
<211> LENGTH: 516
<212> TYPE: DNA
<213> ORGANISM: Artificial Sequence
<220> FEATURE:
<223> OTHER INFORMATION: Synthetic polynucleotide

<400> SEQUENCE: 29
ggatccatgg taagtaaggg ggaggaggac aacatggcga taatcaagga gttcatgcgc       60
ttcaaggttc acatggaggg gtctgtcaac ggccacgagt ttgagatcga gggcgaaggg      120
gagggaagac cttacgaggg aacccagacc gcaaagctaa aggtgacaaa aggtggccct      180
ttgcccttcg cctgggatat actgtcccct cagttcatgt acgggtcgaa ggcctacgta      240
aagcacccag ctgacatccc ggactacttg aagctgtcct ttcccgaggg cttcaagtgg      300
gaacgcgtga tgaacttcga ggacggtggc gtggtgacag tcacacagga ttccagtctg      360
caggacggcg agttcatcta caaggtgaag ttgcggggca caaactttcc ctccgacgga      420
cccgtcatgc agaaaaagac catgggctgg gaggcctctt ccgagagaat gtatcccgaa      480
gacggcgccc tcaagggcga aatcaagcag ccgcgg                                516

<210> SEQ ID NO 30
<211> LENGTH: 26
<212> TYPE: DNA
<213> ORGANISM: Artificial Sequence
<220> FEATURE:
<223> OTHER INFORMATION: Synthetic polynucleotide (primer)

<400> SEQUENCE: 30
gggatccatg gtaagtaagg gggagg                                           26

<210> SEQ ID NO 31
<211> LENGTH: 26
<212> TYPE: DNA
<213> ORGANISM: Artificial Sequence
<220> FEATURE:
<223> OTHER INFORMATION: Synthetic polynucleotide (primer)

<400> SEQUENCE: 31
gccgcggctg cttgatttcg cccttg                                           26

<210> SEQ ID NO 32
<211> LENGTH: 516
<212> TYPE: DNA
<213> ORGANISM: Artificial Sequence
<220> FEATURE:
<223> OTHER INFORMATION: Synthetic polynucleotide

<400> SEQUENCE: 32
ggtaccctgc ttgatttcgc ccttgagggc gccgtcttcg ggatacattc tctcggaaga       60
ggcctcccag cccatggtct ttttctgcat gacgggtccg tcggagggaa agtttgtgcc      120
ccgcaacttc accttgtaga tgaactcgcc gtcctgcaga ctggaatcct gtgtgactgt      180
caccacgcca ccgtcctcga agttcatcac gcgttcccac ttgaagccct cgggaaagga      240
cagcttcaag tagtccggga tgtcagctgg gtgctttacg taggccttcg accgtacat      300
```

```
gaactgaggg gacagtatat cccaggcgaa gggcaaaggg ccaccttttg tcacctttag    360
ctttgcggtc tgggttccct cgtaaggtct tccctcccct tcgccctcga tctcaaactc    420
gtggccgttg acagacccct ccatgtgaac cttgaagcgc atgaactcct tgattatcgc    480
catgttgtcc tcctcccct tacttaccat gagctc                              516

<210> SEQ ID NO 33
<211> LENGTH: 26
<212> TYPE: DNA
<213> ORGANISM: Artificial Sequence
<220> FEATURE:
<223> OTHER INFORMATION: Synthetic polynucleotide (primer)

<400> SEQUENCE: 33
ggagctcatg gtaagtaagg gggagg                                         26

<210> SEQ ID NO 34
<211> LENGTH: 26
<212> TYPE: DNA
<213> ORGANISM: Artificial Sequence
<220> FEATURE:
<223> OTHER INFORMATION: Synthetic polynucleotide (primer)

<400> SEQUENCE: 34
gggtaccctg cttgatttcg cccttg                                         26

<210> SEQ ID NO 35
<211> LENGTH: 531
<212> TYPE: DNA
<213> ORGANISM: Artificial Sequence
<220> FEATURE:
<223> OTHER INFORMATION: Synthetic polynucleotide

<400> SEQUENCE: 35
ggatccctgg agcgtgtgtc ttgcctggag gcgcactctg actatctgcg gtccctggcc    60
gtccacccga gtgagcccct ggtcctctcc tcctcggacg acatgctcat taagctctgg   120
aactgggaca aggcctgggc ctgtgaacag gtcttcgagg acacacgca ctacataatg    180 caagtggtca tcaaccccaa ggacaacaac acttttgcct ccgcctcttt ggaccgcacc   240
atcaaggtct ggcacttggg cgcatcttgc cccaacttca ctctggaggg acatgacaag   300
ggcgtcaact gtctggacta ctaccacgcc ggggacaagc cctacctcat ctcggggca   360 gacgatcgct ccgtcaagat tgggattat cagaataaga attgcgtgca aaccctggaa   420
ggacacgccc aaaacatagc gtctgtgtgt ttccatccag agctcccat aatcttgact   480 gggtctgagg atggaacggt acggatctgg catgcaagta catatccgcg g            531

<210> SEQ ID NO 36
<211> LENGTH: 664
<212> TYPE: DNA
<213> ORGANISM: Artificial Sequence
<220> FEATURE:
<223> OTHER INFORMATION: Synthetic polynucleotide

<400> SEQUENCE: 36
gaattcggaa acaaaatgaa catgttttta aaattgtaag gaaccattct taccctacgt    60
atagaagaaa acatgtgtca gaatgccggc ataaaacgat cacacaaggt acgttgcggc   120
taaagtgcaa tacgtaccca tatgtacttg catgccagat ccgtaccgtt ccatcctcag   180
acccagtcaa gattatgggg agctctggat ggaaacacac agacgctatg ttttgggcgt   240
gtccttccag ggtttgcacg caattcttat tctgataatc ccaaatcttg acggagcgat   300
```

```
cgtctgcccc cgagatgagg tagggcttgt ccccggcgtg gtagtagtcc agacagttga    360
cgcccttgtc atgtccctcc agagtgaagt tggggcaaga tgcgcccaag tgccagacct    420
tgatggtgcg gtccaaagag gcggaggcaa aagtgttgtt gtccttgggg ttgatgacca    480
cttgcattat gtagtgcgtg tgtccctcga agacctgttc acaggcccag gccttgtccc    540
agttccagag cttaatgagc atgtcgtccg aggaggagag gaccaggggc tcactcgggt    600
ggacggccag ggaccgcaga tagtcagagt gcgcctccag gcaagacaca cgctccaggg    660
tacc                                                                 664
```

<210> SEQ ID NO 37
<211> LENGTH: 4095
<212> TYPE: DNA
<213> ORGANISM: Artificial Sequence
<220> FEATURE:
<223> OTHER INFORMATION: Synthetic polynucleotide

<400> SEQUENCE: 37

```
gggctgcagg acgcaatgga ggattatcac cgcaaaaatg aacttcgaaa aaaactttcg     60
agcgaccatg gaaaggagg atcagattca gattacaaca gtggattgct ctggtagcaa    120
atatcttctg ctagattggc tcatggtcgg ttttggacgt tcgaagctca ccgtcaaaag    180
aaacaaaaga gaagaatgac gtcttcgtga cgtagaatct acgactgtac tcggatctgg    240
gaaatgaatt gactcacggt cttcttcgag tcctgttaca ggcccttggt ccgaaccccc    300
acacgatttt tgcaccaaag atttgcttca atttgctgga tgttttgact gcaagatcag    360
ctggcctagc aagagtgctc gtgttgcttc gtcgggaatc cctacgaatt tcagttctgc    420
acaaatttgt ctgccgtttc gagaattcga tatcatcgac taattcgagc tcggtacccg    480
gggatcctct agagtcgacc tgcaggcatg caagcttcag aagcgtgcta tcgaactcaa    540
ccagggacgt gcggcacaaa tgggcatcct tgctctcatg gtgcacgaac agttgggagt    600
ctctatcctt ccttaaaaat ttaatttttca ttagttgcag tcactccgct ttggtttcac    660
agtcaggaat aacactagct cgtcttcacc atgatgcca atctcgccta ttcatggtgt    720
ataaaagttc aacatccaaa gctagaactt ttggaaagag aaagaatatc cgaatagggc    780
acggcgtgcc gtattgttgg agtggactag cagaaagtga ggaaggcaca ggatgagttt    840
tctcgagaca taccttcagc gtcgtcttca ctgtcacagt caactgacag taatcgttga    900
tccggagaga ttcaaaattc aatctgtttg gacctggata agacacaaga gcgacatcct    960
gacatgaacg ccgtaaacag caaatcctgg ttgaacacgt atccttttgg gggcctccgc   1020
tacgacgctc gctccagctg gggcttcctt actatacaca gcgcgcatat ttcacggttg   1080
ccagatgtca agatggccaa gttgaccagt gccgttccgg tgctcaccgc gcgcgacgtc   1140
gccggagcgg tcgagttctg gaccgaccgg ctcgggttct cccgggactt cgtggaggac   1200
gacttcgccg gtgtggtccg ggacgacgtg accctgttca tcagcgcggt ccaggaccag   1260
gtggtgccgg acaacaccct ggcctgggtg tgggtgcgcg gcctggacga gctgtacgcc   1320
gagtggtcgg aggtcgtgtc cacgaacttc cggacgcct ccgggccggc catgaccgag   1380
atcggcgagc agccgtgggg gcgggagttc gccctgcgcg acccgccgg caactgcgtg   1440 cacttcgtgg ccgaggagca ggactgaacc ttccttaaaa atttaatttt cattagttgc   1500
agtcactccg ctttggtttc acagtcagga ataacactag ctcgtcttca ccatggatgc   1560
caatctcgcc tattcatggt gtataaaagt tcaacatcca aagctagaac ttttggaaag   1620
```

```
agaaagaata tccgaatagg gcacggcgtg ccgtattgtt ggagtggact agcagaaagt    1680
gaggaaggca caggatgagt tttctcgagg ccggtctccc tatagtgagt cgtattaatt    1740
tcgataagcc aggttaacct gcattaatga atcggccaac gcgcggggag aggcggtttg    1800
cgtattgggc gctcttccgc ttcctcgctc actgactcgc tgcgctcggt cgttcggctg    1860
cggcgagcgg tatcagctca ctcaaaggcg gtaatacggt tatccacaga atcaggggat    1920
aacgcaggaa agaacatgtg agcaaaaggc cagcaaaagg ccaggaaccg taaaaaggcc    1980
gcgttgctgg cgtttttcca taggctccgc cccnctgacg agcatcacaa aaatcgacgc    2040
tcaagtcaga ggtggcgaaa cccgacagga ctataaagat accaggcgtt ccccctgga    2100 agctccctcg tgcgctctcc tgttccgacc ctgccgctta ccggatacct gtccgccttt    2160
ctcccttcgg gaagcgtggc gctttctcaa tgctcacgct gtaggtatct cagttcggtg    2220
taggtcgttc gctccaagct gggctgtgtg cacgaacccc ccgttcagcc cgaccgctgc    2280
gccttatccg gtaactatcg tcttgagtcc aacccggtaa gacacgactt atcgccactg    2340
gcagcagcca ctggtaacag gattagcaga gcgaggtatg taggcggtgc tacagagttc    2400
ttgaagtggt ggcctaacta cggctacact agaaggacag tatttggtat ctgcgctctg    2460
ctgaagccag ttaccttcgg aaaaagagtt ggtagctctt gatccggcaa acaaaccacc    2520
gctggtagcg gtggtttttt tgtttgcaag cagcagatta cgcgcagaaa aaaggatct    2580 caagaagatc ctttgatctt ttctacgggg tctgacgctc agtggaacga aaactcacgt    2640
taagggattt tggtcatgag attatcaaaa aggatcttca cctagatcct tttaaattaa    2700
aaatgaagtt ttaaatcaat ctaaagtata tatgagtaaa cttggtctga cagttaccaa    2760
tgcttaatca gtgaggcacc tatctcagcg atctgtctat ttcgttcatc catagttgcc    2820
tgactccccg tcgtgtagat aactacgata cgggagggct taccatctgg ccccagtgct    2880
gcaatgatac cgcgagaccc acgctcaccg gctccagatt tatcagcaat aaaccagcca    2940
gccggaaggg ccgagcgcag aagtggtcct gcaactttat ccgcctccat ccagtctatt    3000
aattgttgcc gggaagctag agtaagtagt tcgccagtta atagtttgcg caacgttgtt    3060
gccattgcta caggcatcgt ggtgtcacgc tcgtcgtttg gtatggcttc attcagctcc    3120
ggttcccaac gatcaaggcg agttacatga tcccccatgt tgtgcaaaaa agcggttagc    3180
tccttcggtc ctccgatcgt tgtcagaagt aagttggccg cagtgttatc actcatggtt    3240
atggcagcac tgcataattc tcttactgtc atgccatccg taagatgctt ttctgtgact    3300
ggtgagtact caaccaagtc attctgagaa tagtgtatgc ggcgaccgag ttgctcttgc    3360
ccggcgtcaa tacgggataa taccgcgcca catagcagaa ctttaaaagt gctcatcatt    3420
ggaaaacgtt cttcggggcg aaaactctca aggatcttac cgctgttgag atccagttcg    3480
atgtaaccca ctcgtgcacc caactgatct tcagcatctt ttactttcac cagcgtttct    3540
gggtgagcaa aaacaggaag gcaaaatgcc gcaaaaaagg gaataagggc gacacggaaa    3600
tgttgaatac tcatactctt cctttttcaa tattattgaa gcatttatca gggttattgt    3660
ctcatgagcg gatacatatt tgaatgtatt tagaaaaata aacaaatagg ggttccgcgc    3720
acatttcccc gaaaagtgcc acctgacgtc taagaaacca ttattatcat gacattaacc    3780
tataaaaata ggcgtatcac gaggcccttt cgtctcgcgc gtttcggtga tgacggtgaa    3840
aacctctgac acatgcagct cccggagacg gtcacagctt gtctgtaagc ggatgccggg    3900
agcagacaag cccgtcaggg cgcgtcagcg ggtgttggcg ggtgtcgggg ctggcttaac    3960
tatgcggcat cagagcagat tgtactgaga gtgcaccata tggacatatt gtcgttagaa    4020
```

```
cgcggctaca attaatacat aaccttatgt atcatacaca tacgatttag gtgacactat    4080
agaaccagat ccccc                                                    4095
```

TRANSGENIC MICROALGAE AND USE THEREOF AS A FEED FOR DELIVERY OF INTERFERING RNA MOLECULES

CROSS REFERENCE TO RELATED APPLICATIONS

This application is a Continuation Application of U.S. application Ser. No. 15/741,898, filed on Jan. 4, 2018; which is a 371 of PCT International Application No. PCT/IL2016/050760, filed on Jul. 14, 2016; which claims priority to U.S. application Ser. No. 62/192,082, filed on Jul. 14, 2015, which are hereby incorporated by reference in their entirety

SEQUENCE LISTING

The Sequence Listing submitted herewith as an ASCII text file (2020-08-26_Sequence_Listing.txt, created on Aug. 25, 2020, 19,723 bytes) via EFS-Web is hereby incorporated by reference.

FIELD OF THE INVENTION

The present invention relates to non-propagating transgenic microalgae comprising heterologous RNA interfering (RNAi) molecules and use thereof for delivery of the RNAi molecules to a target organism consuming the transgenic microalgae or via intervening organism that is fed with or exposed to the microalgae expressing the RNAi molecule, particularly for biological control of animal or plant pests.

BACKGROUND OF THE INVENTION

RNA interference (RNAi) is a phenomenon in which double stranded RNA (dsRNA), composed of sense RNA and antisense RNA homologous to a certain region of a target gene affects the cleavage of the target gene transcript, resulting in inhibition of its function. It was discovered in the nematode *Caenorhabdtitis elegans* (Guo, S. and Kemphues, K. J. 1995. Cell 81:611-620) and was later shown to exist in *Trypanosoma brucei, Drosophila, Neurospora*, plants and mammalian cells (Wianny, F. and Zernicka-Goetz, M. 2000. Nat Cell Biol 2:70-75; Cogoni C. 2000. Curr Opin Genet Dev 10(6):638-43; Kennerdell. 2000. Nat Biotechnol August; 18(8):896-8).

RNAi is controlled by the RNA-induced silencing complex (RISC) and is initiated by dsRNA molecules in a cell cytoplasm. The source of the dsRNA molecules can be exogenous or endogenous. The Dicer enzyme cleaves the dsRNA molecules into short double stranded fragments of ~20 nucleotides that are called small interfering RNAs (siRNAs). These short polymers induce the cleavage of complementary mRNAs.

RNAi has been proved to be a very promising tool in several research fields, for example in genomics for gene function determination and gene knockdown in eukaryotes. In biotechnology it shows great potential because of its high specificity enabling its use in medicine for specific control of cancers and viral diseases and in pest control in agriculture and aquaculture.

Microalgae (single cell alga or phytoplankton) represent the largest, but most poorly understood, kingdom of microorganisms on earth. Like plants are to terrestrial animals, the microalgae represent the natural nutritional base and primary source of all the phytonutrients in the aquatic food chain. Algae can serve as an efficient platform for the production of bioactive molecules, including genetically engineered enzymes, vaccines or other proteins. The produced molecules can be extracted from the microalgae or can be orally delivered within the microalgae to the target organisms. Expression of recombinant proteins in algae has been reported, and various methods are available for production of exogenous proteins within the algae cells, including expression within the cell plastid.

U.S. Application Publication No. 2008/0107652 discloses the use of transgenic microalgae for prevention, amelioration or treatment of diseases in aquatic animals. The transgenic algae are fed to the aquatic animal directly or indirectly. This system is proposed for delivering immunogenic peptides, single chain antibody fragments, and DNA vaccines.

Nucleic acid molecules have emerged as versatile tool with promising utility in a variety of biochemical, diagnostic and therapeutic applications. However, the use of these molecules is still scarce due to the lack of efficient delivery systems. A successful development of nucleic acid delivery system through feeding is challenged by a variety of barriers, one of the most significant being the intestinal mucosa. The intestinal mucosa serves as both a physical and a biochemical barrier, separating the external environment from the internal milieu of the body.

U.S. Pat. No. 8,633,028 discloses dsRNA induced specific and non-specific immunity in crustaceans and other invertebrates. The system and methods provided include the treatment of shrimp with dsRNA targeted to viruses that infect the shrimp. In one illustrated embodiment, dsRNA that was injected to the Marine Shrimp *Litopenaeus vannamei* blocked viral infection.

Parenteral administration of nucleic acids by injection is, however inconvenient because of the risks involved and further because of the recipient's pain and fear. Various other methods have been suggested for parenteral administration of nucleic acids. For example, U.S. Pat. No. 8,524,679 discloses methods of delivering nucleic acids, including dsRNA, to mammalian target cells in vivo via intercellular transfer. The delivery of the nucleic acid is through direct transfection of the animal cells. U.S. Pat. No. 8,445,456 discloses the use of nucleic acid molecule mediating RNA interference for treating or reducing pain. The invention however discloses that the nucleic acid molecule is administrated to a patient by injection. When the target organisms are aquatic animals or a large number of land animals, parenteral administration is practically impossible.

Additional modes of application of RNAi agents have been tested. For example, U.S. Pat. No. 8,404,832 discloses the oral administration of siRNA, wherein the siRNA strands are chemically modified.

Another example for oral delivery is demonstrated in transgenic plants harboring dsRNA designed to target specific genes in the parasitic nematode (*Meloidogyne incognita*). Once invading into the transgenic plant cells, the nematodes consume its cytoplasm and die, due to the RNAi activity of the dsRNA. The transgenic plants are therefore highly resistant to the nematode (Yadav et al, Mol Biochem Parasitol. 2006. 148(2):219-22, Klink et al. Planta. 2009. 230(1):53-71).

The feasibility of using RNAi for protecting crop plants from insect herbivores has been demonstrated (Price D R and Gatehouse J A. 2008. Trends in Biotechnology 26(7): 393-400; Katoch R. et al., 2013. Appl Biochem Biotechnol 171:847-873). The method has relied on the injection of double-stranded RNA (dsRNA) into the insect haemoceol, which is not practical in field conditions, or on direct feeding of the dsRNA in the diet, posing the problem of dsRNA instability. Therefore development of a robust dsRNA feeding methodology in insects is a prerequisite for utilization of this technology.

U.S. Application Publication No. 2013/0315883 discloses the expression of silencing RNA in transgenic plants, including microalgae for genetic control of parasites and pathogens. The invention exploits the ability of plants to express the silencing RNA in a form within chloroplasts that is efficiently taken up, after ingestion where it can act to suppress the expression of target genes within the pathogen or parasite.

One of the major drawbacks in the field of transgenic plants is the need to have specific means for the production of each transgenic crop type, while one type of transgenic algae may be used to protect any desired crop. In addition, there is a growing public concern regarding the effect of genetically modified plants and algae on the environment. The reproducible nature of plant and algae may lead to their spread into natural environments contaminating wild type species with foreign genes.

The circadian clocks govern many metabolic and behavioral processes in an organism. In insects, these clocks and their molecular machinery have been found to influence reproduction in many different ways. Reproductive behavior including courtship, copulation and egg deposition, is under strong influence of the daily rhythm (Tobback J. et al., 2011. Insect Biochemistry and Molecular Biology 41(5):313-321). One of the core genes in the circadian regulation network in mammals and insects is designated "clock" (clk). In contrast to other insects, injection of double-stranded RNA (dsRNA) targeted to silence the clk gene is lethal in adults and fifth instar nymphs of the desert locust, *Schistocerca gregaria*, in a dose dependent manner. clk-knocked down fifth instar nymphs are able to undergo their imaginal molt but, depending on the amount of dsRNA, it takes them longer than the controls to reach adulthood. As adults, clk-knocked down animals do not develop their fat body and ovaries like the control animals (Tobback J et. al 2012. Insect Molecular Biology 21(3):369-381.

Administration of nucleic acid molecule mediating RNAi through feeding is one of the most desirable approaches for gene silencing; however the practicability of this delivery method still remain a challenge mainly due to instability of the RNAi molecule and to safety issues. Thus, there is a great need for and it would be highly advantageous to have an oral delivery system that is easy for production and use, maintains the biological activity of the RNAi molecules and facilitate absorption of the biologically active molecules systemically without having negative effect on the environment.

SUMMARY OF THE INVENTION

The present invention provides preparations of non-propagating microalgae for oral delivery of nucleic acid molecules mediating RNAi to an organism, providing for the systemic absorption of the RNAi molecule by the organism. In particular, the present invention provides preparations of dried transgenic microalgae comprising at least one heterologous RNAi molecule targeted to a polynucleotide present in a cell of a target organism other than the microalgae. The organism can be aquatic or land animal including insect pests. When the transgenic microalgae are consumed by the aquatic or land animal, the RNAi molecule silences the target polynucleotide. Additionally, the microalgae can be provided to the aquatic or land animal via intervening organism that is fed with or exposed to the microalgae expressing the RNAi molecule. In particular exemplary embodiments, in the case of plant pests, particularly insects, the plant may be at least partially coated with the non-propagating transgenic microalgae comprising RNAi molecule targeted to silence a pest gene.

In other alternative embodiments, the RNAi molecule can be targeted to inhibit the expression of gene(s) having deleterious effects on the target animal. If it inhibits a gene that has deleterious effects to the target animal it improves the survival and welfare of that animal.

The microalgae RNAi delivery preparations of the present invention are advantageous over hitherto known RNAi expressing microalgae in that the microalgae cells are not alive and cannot propagate, and thus do not pose any risk of spreading genetically engineered organisms in the environment.

According to some embodiments the non-propagating microalgae comprising the RNAi molecule are used as an animal food or food additive applicable for feeding animals or as a part of the pest natural food.

The heterologous RNAi molecule is characterized by being biologically active, stable and highly specific once consumed by the xenogeneic target organism, inhibiting the expression of a target gene within said target organism.

The present invention is based in part on the unexpected discovery that dsRNA molecules expressed within dry microalgae can be transferred to an insect consuming the microalgae in an intact and active form. In certain embodiments exemplified herein below, the target gene is an essential gene for the development of an insect, such that silencing of said gene results in inhibition and/or negative alteration of the insect development.

Without wishing to be bound by any theory or mechanism of action, the preserved activity of the RNAi molecule may be attributed to the dsRNA stable structure provided herein and to the drying process. In addition, the microalgal cell wall, specifically the cell wall of the alga *Phaeodactylum tricornutum* serves as a natural encapsulation material which protects the RNAi molecule from being degraded in the digestive track of the target aquatic or land animal, therefore enabling its absorption to the blood or hemolymph of the target animal. The RNAi molecule then inhibits the expression of a target gene within the cells of said animal. An RNAi molecule that remains intact after passing through a developed digestive system of a vertebrate animal or an insect is highly unexpected.

According to one aspect, the present invention provides a non-propagating transgenic microalga comprising at least one heterologous RNAi molecule, wherein the RNAi molecule is targeted to a polynucleotide present within a xenogeneic organism and wherein said RNAi molecule silences the expression of the polynucleotide present within the xenogeneic organism when the microalga is consumed by said xenogeneic organism or by a host of said xenogeneic organism.

According to certain embodiments, the non-propagating transgenic microalga is in a dried form. According to certain exemplary embodiments, the transgenic microalgae are dried using freeze-drying or microwave vacuum drying methods.

According to certain embodiments, the non-propagating transgenic microalga comprises multiple copies of the RNAi molecule.

According to certain exemplary embodiments, the RNAi molecule is transcribed within the microalgae nucleus.

According to certain embodiments, the RNAi molecule comprises a sense strand and an antisense strand, the sense strand and the antisense strand together form a duplex, said sense strand comprises at least 19 contiguous nucleic acids having at least 95% identity to the target polynucleotide present within the xenogeneic organism. According to additional embodiments, the at least 19 contiguous nucleic acids comprise 1, 2, 3, or 4 substitutions when compared to the target polynucleotide present within the xenogeneic organism. Each possibility represents a separate embodiment of the invention.

According to certain embodiments, the sense strand and antisense strand each comprises from about 20 to about 1500 nucleotides in length. Alternatively, the sense strand and antisense strand each comprises from about 50 to about 1000 nucleotides in length, further alternatively each strand comprises from about 100 to about 800 nucleotides, yet further alternatively each strand comprises from about 150 to about 500 nucleotides in length.

According to certain embodiments, the sense and the antisense strands are separated by a linker sequence. According to certain exemplary embodiments, the linker sequence is an intron sequence. According to some embodiments, the intron is from the microalgae *Phaeodactylum tricornutum*, having the nucleic acid sequence set forth is SEQ ID NO:6. According to additional certain exemplary embodiment, the total length of the RNAi molecule is from about 1,000 bp to about 1,500 bp. According to currently certain exemplary the total length of the RNAi molecule is about 1200 bp. Without wishing to be bound by any specific theory or mechanism of action, the presence of the intron and the total length of the RNAi molecule contribute to the unexpected stability of the RNAi molecule during the processing of the microalgae, particularly during drying, and during its consumption by the target organism such that it can exert its silencing activity towards a gene of the target organism or an exogenous gene present therein.

Various microalgae species can be used according to the teachings of the present invention, as long as the microalgae maintain or regenerate their cell wall structure after transformation. According to certain exemplary embodiments, the microalga is eukaryotic. According to certain embodiments, the microalga is a marine microalga.

According to certain embodiments, the marine microalga is selected from the group consisting of, but not restricted to, *Phaeodactylum tricornutum; Dunaliella* spp.; *Nannochloropsis* spp. including *Nannochloropsis oculata, Nannochloropsis sauna, Nannochloropsis gaditana; Nannochloris* spp., *Tetraselmis* spp. including *Tetraselmis suecica, Tetraselmis chuii; Isochrysis galbana; Pavlova* spp.; *Amphiprora hyaline; Chaetoceros muelleri*; and *Neochloris oleoabundans*. Each possibility represents a separate embodiment of the present invention.

According to certain exemplary embodiments, the microalga is selected from the group consisting of *Phaeodactylum tricornutum, Nannochloris* spp., *Nannochloropsis* spp. and *Dunaliella* spp.

According to certain currently exemplary embodiments, the microalga is *Phaeodactylum tricornutum*. Without wishing to be bound by any specific theory or mechanism of action, the silicified wall of *P. tricornutum* may act as a form of encapsulation that protect the RNAi molecules expressed within the algal cells from the outside harsh environment throughout the growth, harvest and processing of the algal biomass and further from the environment of the gastrointestinal tract of the animal consuming the algae.

According to certain embodiments, the target polynucleotide present within the xenogeneic organism is an endogenous gene of said organism.

According to certain embodiments, the xenogeneic organism is a pest. According to these embodiments, the RNAi molecule silences the expression of a gene which is essential for the pest growth and/or redevelopment, wherein said silencing has a deleterious effect on said pest. According to certain exemplary embodiments, the pest is a plant pest. According to certain exemplary embodiments, the plant pest is an insect attacking crop plants, forest plants (specifically trees), ornamental plants or any combination thereof.

According to some embodiments, the insect belongs to the order Orthoptera. According to other embodiments, the insect is a desert locust (*Schistocerca gregaria*). According to other embodiments, the insect is a migratory locust (*Locusta migratoria*). According to some embodiments, the insect belongs to the order Lepidoptera. According to certain exemplary embodiment, the Lepidoptera is *prodenia*. According to other exemplary embodiments the *prodenia* is the leafworm *Spodoptera littoralis*. According to other embodiments the insect belongs to the order Coleoptera. According to exemplary embodiment, the Coleoptera is a beetle. According to certain exemplary embodiments the beetle is the meal worm beetle *Tenebrio molitor*.

According to other embodiments, the pest is an animal pest. According to some embodiments, the animal is an aquaculture animal. According to certain exemplary embodiments, the aquaculture animal is selected from fish and crustacean.

According to additional embodiments, the animal is a land animal. According to certain exemplary embodiments, the land animal is selected from a farm animal and a pet.

According to other embodiments, silencing of the target endogenous gene in a xenogeneic organism has a beneficial effect for plants, particularly crop plant or for animals that are damaged by said xenogeneic organism. According to these embodiments, silencing of the target endogenous gene in the organism has a deleterious effect on at least one of the growth, development, survival, health and welfare of the organism that consumes the microalgae, such that the microalgae or a composition comprising same may be referred to as a pesticide. Each possibility represents a separate embodiment of the present invention.

According to certain embodiments, the xenogeneic organism is the insect migratory locust (*Locusta migratoria*). According to certain embodiments, the xenogeneic organism is the insect desert locust (*Schistocerca gregaria*). According to certain exemplary embodiments, the RNAi molecule is targeted towards the desert locust (*Schistocerca gregaria*) clk gene, resulting in disturbed development and/or death of the locust. According to certain embodiments, the RNAi molecule is targeted to the clk gene of the desert locust comprising the nucleic acids sequence set forth in SEQ ID NO:1. According to certain exemplary embodiments, the RNAi molecule comprises a sense strand comprising the nucleic acids sequence set forth in SEQ ID NO:2 or a fragment thereof, and an antisense strand essentially complementary to said SEQ ID NO:2 or a fragment thereof. According to certain exemplary embodiments, the RNAi molecule comprises a sense strand comprising the nucleic acids sequence set forth in SEQ ID NO:2; a linker sequence comprising the nucleic acid sequence set forth in SEQ ID NO:6; and an antisense strand comprising the nucleic acid sequence set forth in SEQ ID NO:3.

According to certain exemplary embodiments, the present invention provides a non-propagating transgenic microalga comprising an RNAi molecule targeted to clk gene of desert locust, wherein the clk gene comprising the nucleic acids sequence set forth in SEQ ID NO:1. According to additional exemplary embodiments, the present invention provides a non-propagating transgenic microalga comprising an RNAi molecule comprising a sense strand comprising the nucleic acids sequence set forth in SEQ ID NO:2; a linker sequence comprising the nucleic acid sequence set forth in SEQ ID NO:6; and an antisense strand comprising the nucleic acid sequence set forth in SEQ ID NO:3.

According to other embodiments, the polynucleotide present within the xenogeneic organism is heterologous gene to said organism. According to certain exemplary embodiments, the heterologous polynucleotide is of a virus infecting the xenogeneic organism and the RNAi molecule is targeted to silence a viral gene.

According to certain exemplary embodiments, the xenogeneic organism is a crustacean and the heterologous polynucleotide is of the white spot syndrome virus (WSSV).

According to yet additional embodiments, the xenogeneic organism is a pathogen and the non-propagating transgenic microalgae are consumed by a host of the pathogen.

According to theses embodiments, the RNAi molecule is targeted to a polynucleotide of the pathogen as to silence its expression.

According to exemplary embodiments, silencing the pathogen polynucleotide has a deleterious effect on the growth and/or proliferation and/or development of the pathogen, thus having a positive effect on at least one of the growth, development, survival, welfare and health of the host organism infected by the pathogen.

According to certain embodiments, the pathogen is selected from the group consisting of a parasite and a bacterium.

According to certain exemplary embodiments the infected host is an aquaculture organism. According to certain embodiments, the aquaculture organism is selected from fish and crustacean. According to certain exemplary embodiments, the target pathogen is a copepod of the order Siphonostomatoida. According to other embodiments, the copepod is of the class Caligidae. According to yet additional embodiments, the copepod is *Lepeophtheirus salmonis*, marine ectoparasites that feed on the mucus, epidermal tissue, and blood of host marine fish, among them fish of the Salmonidae.

According to yet other embodiments, the infected host is selected from the group consisting of domestic farm animal and a pet. Each possibility represents a separate embodiment of the present invention.

According to some embodiments, the farm animal is poultry and the parasite is of the family Menoponidae. According to certain exemplary embodiments, the poultry parasite is selected from the group consisting of *Menacanthus stramineus* and *Menopon gallinae*.

According to certain embodiments, the expression of the target gene or polynucleotide is being inhibited by at least 10%, 30%, 50%, 70%, 90%, 99% or more when compared to the expression of the same target gene or polynucleotide in an organism not consuming the transgenic microalga.

According to yet additional embodiments, the RNAi molecule is an siRNA. According to some embodiments, the heterologous polynucleotide expressing siRNA comprises a sense sequence of about 20-25 nucleic acids in length and antisense sequence complementary to said 20-25 nucleic acids.

According to yet other embodiments, the RNAi molecule of the present invention is incorporated into a DNA construct enabling its expression in the microalga. According to one embodiment, the DNA construct comprises at least one expression regulating element selected from the group consisting of a promoter, an enhancer, an origin of replication, a transcription termination sequence and the like.

According to some embodiments, the DNA construct comprises a promoter. The promoter can be constitutive or induced as is known in the art. According to typical embodiments, the promoter is a constitutive promoter operable in microalgae. According to other embodiments, the DNA construct further comprises transcription termination sequence signal. According to certain embodiments, the polynucleotide that encodes for the RNAi molecule is operably linked to a single promoter located upstream to both sense and anti-sense strands. According to certain embodiments, each strand of the RNAi molecule is encoded by a polynucleotide that has its own promoter. According to some embodiments, each promoter is operably linked and located upstream to a polynucleotide that encodes for each of the sense and antisense strands. According to certain embodiments, each strand is transcribed from a different DNA construct.

According to certain embodiments, the microalgae of the present invention can be administered and consumed per se, or can be formulated into an edible composition further comprising edible diluents, excipients or carriers. The term "edible" is used herein in its broadest scope and includes compositions that may be consumed by aquatic animals and by plant and animal pests, including insects. The microalgae or the composition comprising same can be further used as a food additive.

According to certain embodiments, the algae-based edible formulation is an animal food composition, including food compositions for aquaculture.

According to some embodiments, the algae-based edible composition is formulated to cover, at least partially, the food source of the xenogeneic organism. According to certain exemplary embodiments, the organism is plant insect or a plant parasite and the algae-based edible composition at least partially covers the plant.

According to certain embodiments, the xenogeneic organism belongs to the order Orthoptera. According to yet other embodiments, the organism belongs to the order Lepidoptera. According to yet additional embodiments, the organism belongs to the order Coleoptera.

According to yet additional embodiments, the organism belongs to the phylum Nematoda.

According to yet other embodiments, the-algae based edible formulation serves as a food source for a host of an animal pathogen, including animal parasite, wherein the RNAi molecule is targeted to a polynucleotide of the animal pathogen. According to some embodiments, the animal pathogen is the sea lice parasite and the host is salmon fish. According to other embodiments, the host is an aquaculture or land animal and the animal pathogen is a virus or a bacterium.

According to certain embodiments, the microalgae are formulated in the form of a spray suspension. According to some embodiments the spray suspension is sprayed on crop plants. According to some embodiments the spray suspension is sprayed on the plant leaves. According to certain embodiments, the suspension is sprayed on edible plant parts such as fruit. According to other embodiments, the microalgae suspension is sprayed on wheat seedlings.

According to an additional aspect, the present invention provides a method for oral delivery of an RNAi molecule to an organism, the method comprising orally administering to the organism a non-propagating transgenic microalga comprising a polynucleotide expressing an RNAi molecule, wherein the RNAi molecule silences the expression of a gene or a part thereof present within the organism.

The organism is any of the organisms as described hereinabove.

According to certain exemplary embodiments, the present invention provides a method for silencing clk gene of desert locust, the method comprises orally delivering to the desert locust non-propagating transgenic microalgae comprising an RNAi molecule targeted to the clk gene, said clk gene comprises the nucleic acids sequence set forth in SEQ ID NO:1. According to additional exemplary embodiments, the present invention provides a method for silencing clk gene of desert locust, the method comprises orally delivering to the desert locust a non-propagating transgenic microalgae comprising an RNAi molecule comprising a sense strand comprising the nucleic acids sequence set forth in SEQ ID NO:2; a linker sequence comprising the nucleic acid sequence set forth in SEQ ID NO:6; and an antisense strand comprising the nucleic acid sequence set forth in SEQ ID NO:3.

The microalga is any of the microalgae as described hereinabove. According to certain embodiments, the non-propagating transgenic microalgae are in a dried form.

According to some embodiments, the non-propagating transgenic microalgae are administered through coverage of the organism food. The composition is formulated for feeding any of the organisms as described hereinabove.

It is to be understood explicitly that the scope of the present invention encompasses homologs, analogs, variants and derivatives, including shorter and longer polynucleotides, as well as RNA and polynucleotide analogs with one or more nucleic acid substitution, as well as nucleic acid derivatives, non-natural nucleic acids and synthetic nucleic acids as are known in the art, with the stipulation that these variants and modifications must preserve the RNAi activity following the consumption of the transgenic algae according to the teaching of the present invention.

Other objects, features and advantages of the present invention will become clear from the following description and drawings.

BRIEF DESCRIPTION OF THE FIGURES

FIG. 1 shows a scheme of the pPhaT expression vector comprising the sense and antisense nucleic acid sequence fragments of clk (dsRNA-Clk).

FIG. 2 shows a scheme of the pPhaT expression vector comprising the sense and antisense of nucleic acid sequence fragments of GFP (dsRNA-GFP).

FIG. 3 shows a scheme of the pPhaT expression vector comprising the sense and antisense of nucleic acid sequence fragments of mCherry (dsRNA-mCherry).

FIG. 4 shows the relative quantification (RQ) of dsRNA targeted to mCherry (dsRNA-mCherry) in the hemolymph of mealworm beetle, *Tenebrio molitor*, which were fed with transgenic algae expressing the dsRNA-mCherry. Total RNA samples were extracted from the hemolymph of *Tenebrio molitor* which were fed with cabbage leaves sprayed with transgenic algae (dsmCherry) or wild type algae (WT) or without algae at all (Mock). The samples were subjected to relative quantification by qRT-PCR analysis with dsRNA-mCherry specific primers. Synthetic RNA (Primer Design) was used as a reference. Analysis was performed using the ΔΔCt method.

FIG. 5 shows relative quantification (RQ) of dsRNA-GFP (dsGFP) and TATA box binding protein (TBP) RNA levels present in *Spodoptera littoralis* hemolymphs. The presence of dsRNA-GFP and TBP was examined in hemolymphs of *Spodoptera littoralis* which were fed with castor oil (*Ricinus communis*) leaves sprayed with transgenic algae expressing dsRNA-GFP. Wild type (WT) algae served as a control.

FIG. 6A and FIG. 6B show relative quantification (RQ) of *Schistocerca gregaria* endogenous clock and period RNA levels in gonads and brains respectively. FIG. 6A shows clock mRNA levels in gonads of young locusts. RNA was extracted from gonads of young adults, after the first molting. Reduction of 36% in clock mRNA levels was detected in locusts fed with algae expressing dsRNA-clock (dsClock) compared to locusts fed with WT algae (p value=0.027). FIG. 6B shows period mRNA levels in brains of adult locusts. RNA was extracted from brains of locusts. Reduction of 27% in period mRNA levels was detected in locusts fed with algae expressing dsRNA-clock-compared to locusts fed with WT algae. The samples were subjected to relative quantification by qRT-PCR analysis with specific primers. GAPDH was used as a housekeeping gene.

FIG. 7A and FIG. 7B show that silencing the clk gene results in reduced number of hatched larvae per egg pod. FIG. 7A shows more than 2 times reduction of hatched eggs in the locusts fed with transgenic microalgae expressing the dsRNA-clock (dsClock), compared to the locusts fed with WT algae. FIG. 7B presents the results of additional experiment showing that the number of larvae hatched from eggs of locusts fed with leaves brushed with transgenic algae expressing dsRNA-clock (specific dsRNA) was lower compared to the number of larvae hatched from eggs of locusts fed with leaves brushed with dsGFP expressing algae (Control dsRNA) throughout the experiment.

FIG. 8A-FIG. 8C show the changes in the motility during feeding between *Schistocerca gregaria* locusts fed with algae expressing dsRNA-clock (dsClock) versus *S. gregaria* locusts fed with WT algae. Locusts were monitored during a 2-hours feeding period and the % of change in motility in each cage was averaged. The number of animals in each cage was 40. Each of FIG. 8A, FIG. 8B and FIG. 8C represents an independent repeat.

FIG. 9 shows that oral delivery of algae expressing dsRNA targeted specifically toward the clk gene affects male/female distribution in *Schistocerca gregaria. S. gregaria* were fed for 27 days with wheat sprouts brushed with either dsclock expressing algae or with dsGFP expressing algae. Adult males and female of 4 independent repeats were counted and the average ratio of male/female animals was calculated (p-value=0.01).

FIG. 10 shows the detection of dsRNA-GFP in hemolymph of crustaceans fed with algae expressing dsRNA-GFP (dsGFP). *Cherax quadricarinatus* crustaceans were fed with feed pellets containing dsRNA-GFP-expressing algae or WT algae. RNA extracted from hemolymph of *Cherax quadricarinatus* was loaded on a membrane and hybridized with DIG-labeled GFP RNA probe. A signal was detected in samples of animals fed with dsRNA-GFP expressing algae (dsGFP), but not in the negative control samples (WT algae). Each spot represents 1% of the hemolymph of the whole animal. Positive control-RNA extracted from dsRNA-GFP-expressing algae. The numbers indicate the total RNA amount (ng) in each spot.

FIG. 11A and FIG. 11B demonstrate the non-viability of algae cells following freeze-drying. FIG. 11A: 1 gram of freeze-dried *Phaeodactylum tricornutum* algae powder (containing $3.42 \times 10^{10}$ cells) was mixed with 9 ml of ASW (Artificial Sea Water). 400 µl of the mixture were plated on either ASW agar plates or in suspension in ASW and maintained for 10 days. FIG. 11B: Fresh *Phaeodactylum*

*tricornutum* algae liquid culture containing equivalent cell number as the freeze-dried algae were plated under similar conditions. Cell growth was monitored after 10 days.

DETAILED DESCRIPTION OF THE INVENTION

The present invention provides compositions and methods for oral delivery of RNAi molecules to a target organism in an efficient, stable and environmentally safe way. In particular, the present invention provides non-propagating transgenic microalgae comprising polynucleotide molecules mediating RNAi and edible compositions comprising same.

The present invention discloses that the RNAi molecule exerts its biological activity in cells or tissues of the organism consuming the transgenic microalgae. The RNAi molecule comprises a sequence that is complementary to a target gene or a part thereof present in the organism consuming the non-propagating transgenic microalgae. Additionally or alternatively, the target gene is present in a pathogen of said organism. As a result, the target gene expression is inhibited. The RNAi may be used for applying a deleterious effect on the organism, for instance when the organism is a pest or when the organism is a pathogen which invades into a host organism and survives within its cell. In addition, the RNAi may have a beneficial effect on the growth, development or welfare of the consuming organism by altering its endogenous genes expression.

The present invention is based in part on the unexpected discovery that the RNAi molecules remain intact throughout the processing of the transgenic microalgae and up to the consumption of the algae by insects. Without wishing to be bound by any particular theory or mechanism of action, the microalgal cell which serves as a natural encapsulation material together with the relatively stable structure of the dsRNA protect the RNAi molecule from being degraded during processing, particularly during drying and further within the digestive system of organism.

Unexpectedly the algae of the invention can be dried and stored while preserving the RNAi activity once the dried algae are consumed by an organism. A significance advantage of the algae-based RNAi delivery system of the invention is that the dried algae of the invention cannot propagate even if re-hydrated, as exemplified in FIG. 11, such that no accidental spread of genetically modified microalgae into a natural environment may occur.

Additional advantage of the technology of the present invention is in that the technology is generic in the sense that the microalgae can be applied to a wide range of target organisms, directly or indirectly via the target organism natural food. No specificity for the target organism (apart from the targeted gene) is required in the genetic engineering process. In contrast, in producing transgenic plants (expressing *Bacillus thuringiensis* for example), there is a need to have the knowledge how to transform each crop individually.

Additional advantage of the present invention is that the algae can be also provided to those animals not consuming the algae as part of their diet, for example by spraying the algae onto regular food of said animals (for example, spraying the transgenic microalgae onto plants consumed by an insect). Additional advantage of the non-propagating transgenic microalgae formulations of the present invention is a long shelf life. According to certain embodiments, the dried transgenic microalgae can be stored at 4° C. for 6-12 months.

Typically, RNA interference (RNAi) refers to the process of sequence-specific post transcriptional gene silencing mediated by small interfering RNAs (siRNA). Long double stranded RNA (dsRNA) in cells typically stimulates the activity of a ribonuclease III enzyme referred to as Dicer. The Dicer is involved in the processing of the long dsRNA into short pieces of siRNA. siRNAs derived from Dicer activity are typically about 21-23 nucleotides in length and include duplexes of about 19 base pairs.

The RNAi response also features an endonuclease complex containing siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex. Without being bound to any mechanism of processing or action, the present invention relates to RNAi, whether processed or not, as a tool for down regulating gene expression.

Definitions

The terms "microalga" or "microalgae" are used herein in their broadest scope and refer to unicellular microscopic eukaryotic algae, typically found in freshwater and marine systems. Depending on the species, the microalgae size can range from a few micrometers (μm) to a few hundreds of micrometers. According to certain currently specific embodiments, the term refers to marine eukaryotic microalga or microalgae.

As used herein, the terms "dry" or "dried" when used with reference to the transgenic microalgae of the present invention refers to microalgae preparation comprising no more than 20% of water, typically no more than 15% of water out of the total mass of the transgenic microalgae.

As used herein, the term "non-propagating" when used with reference to the transgenic microalgae of the present invention refers to microalgae that are not viable in the sense that the microalgae cannot divide and produce offspring.

The terms "RNAi molecule" and "RNA interfering molecule" are used interchangeably herein. These terms encompass double stranded RNA (dsRNA) sequences with sense and antisense strands, wherein the antisense has high complementarity to target genes. The terms also encompass a polynucleotide expressing the dsRNA. The sense and the antisense may have partial or full double stranded character. The double stranded RNA may be cleaved by a Dicer protein into ~20 nucleotides, or the expressed dsRNA may be of a length of ~20 nucleotides, which later induce the cleavage of their complementary mRNA. As a result, the expression of the target gene is reduced.

The terms "down regulated", "inhibited", "reduced" and "silenced" (in any tense used) as referring to genes targeted by the RNAi molecules, refers to a diminishment in the level of expression of a gene(s) in the presence of one or more double stranded RNA(s) or DNA construct(s) expressing same when compared to the level in the absence of such double stranded RNA(s) or DNA construct(s). The terms "down regulated", "inhibited", "reduced", and "silenced" are used herein to indicate that the target gene expression is lowered by 1-100%. For example, the expression may be reduced by about 10, 20, 30, 40, 50, 60, 70, 80, 90, 95, 99%, or more.

The sequence of the double stranded RNA can correspond to the full length target gene, or to a subsequence thereof. Double stranded RNA is "targeted" to a gene in that the nucleotide sequence of the duplex portion of the double stranded RNA is substantially complementary to a nucleotide sequence of the target gene. The double stranded RNA of the invention may be of varying lengths. The length of each strand of the double stranded RNA is preferably from about 20 to about 1500 nucleotides in length. Alternatively, the sense strand and antisense strand each comprises from about 50 to about 1000 nucleotides in length, further alternatively each strand comprises from about 100 to about 800 nucleotides, yet further alternatively each strand comprises from about 150 to about 500 nucleotides in length. However, an RNA strand of about 12 to about 20 nucleotides is also encompassed in the present invention.

The terms "xenogeneic organism" "target organism" and "xenogeneic target organism are used herein interchangeably and refer to an organism other than the transgenic microalgae. According to certain embodiments of the present invention the xenogeneic organism is the organism that consumes the transgenic microalga. The RNAi molecule may be targeted to a polynucleotide of the target organism or to a heterologous polynucleotide within the xenogeneic organism, particularly a virus. According to other embodiments of the present invention, the target organism is a pathogen of a host organism consuming the transgenic microalgae and then the RNAi molecule is targeted to a polynucleotide of the pathogen. According to certain embodiments, the pathogen is a parasite or a bacterium.

The term "gene" in its broadest sense refers to a discrete genomic region whose transcription is regulated by one or more promoters and distal regulatory elements and which contains the information for the synthesis of functional proteins or non-coding RNAs, related by the sharing of a portion of genetic information at the level of the ultimate products (proteins or RNAs). As used herein, the term "gene" refers to a nucleic acid (e.g., DNA or RNA) sequence that comprises coding sequences necessary for the production of RNA or proteins. An RNA or a protein can be encoded by a full-length coding sequence or by any part thereof. The term "parts thereof" when used in reference to a gene refers to fragments of that gene. The fragments may range in size from a few nucleotides to the entire gene sequence minus one nucleotide.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene, wherein a genomic form or clone of a gene contains the coding region interrupted with non-coding sequences termed "introns" or "intervening regions" or "intervening sequences." Introns are removed or "spliced out" from the nuclear or primary transcript, and therefore are absent in the messenger RNA (mRNA) transcript.

As referred to herein, the terms "polynucleotide molecules", "polynucleotide", "nucleic acid" and "nucleotide" sequences may interchangeably be used herein. The terms are directed to polymers of deoxyribonucleotides (DNA), ribonucleotides (RNA), and modified forms thereof in the form of a separate fragment or as a component of a larger construct, linear or branched, single stranded (ss), double stranded (ds), triple stranded (ts), or hybrids thereof. The term also encompasses RNA/DNA hybrids. The polynucleotides may be, for example, sense and antisense oligonucleotide or polynucleotide sequences of DNA or RNA. The DNA or RNA molecules may be, for example, but are not limited to: complementary DNA (cDNA), genomic DNA, synthesized DNA, recombinant DNA, or a hybrid thereof or an RNA molecule such as, for example, mRNA, shRNA, siRNA, miRNA, and the like. Accordingly, as used herein, the terms "polynucleotide molecules", "oligonucleotide", "polynucleotide", "nucleic acid" and "nucleotide" sequences are meant to refer to both DNA and RNA molecules. The terms further include oligonucleotides composed of naturally occurring bases, sugars, and covalent inter nucleoside linkages, as well as oligonucleotides having non-naturally occurring portions, which function similarly to respective naturally occurring portions.

As referred to herein, the term "complementary" is directed to base pairing between strands of nucleic acids. As known in the art, each strand of a nucleic acid may be complementary to another strand in that the base pairs between the strands are non-covalently connected via two or three hydrogen bonds. Two nucleotides on opposite complementary nucleic acid strands that are connected by hydrogen bonds are called a base pair. According to the Watson-Crick DNA base pairing, adenine (A) forms a base pair with thymine (T) and guanine (G) with cytosine (C). In RNA, thymine is replaced by uracil (U). The degree of complementarity between two strands of nucleic acid may vary, according to the number (or percentage) of nucleotides that form base pairs between the strands. For example, "100% complementarity" indicates that all the nucleotides in each strand form base pairs with the complement strand. For example, "95% complementarity" indicates that 95% of the nucleotides in each strand from base pair with the complement strand. The term sufficient complementarity may include any percentage of complementarity from about 30% to about 100%.

The term "about" as used herein in the context of the sequence length refers to within a range of minus or plus 10%.

The term "construct", as used herein refers to an artificially assembled or isolated nucleic acid molecule which may be comprises of one or more nucleic acid sequences, wherein the nucleic acid sequences may be coding sequences (that is, sequence which encodes for an end product), regulatory sequences, non-coding sequences, or any combination thereof. The term construct includes, for example, vectors but should not be seen as being limited thereto.

The term "expression vector" refers to vectors that have the ability to incorporate and express heterologous nucleic acid fragments (such as DNA) in a foreign cell. In other words, an expression vector comprises nucleic acid sequences/fragments (such as DNA, mRNA, tRNA, rRNA), capable of being transcribed. Many viral, prokaryotic and eukaryotic expression vectors are known and/or commercially available. Selection of appropriate expression vectors is within the knowledge of those having skill in the art.

The terms "promoter element", "promoter" or "promoter sequence" as used herein, refer to a nucleotide sequence that is generally located at the 5' end (that is, precedes, located upstream) of the coding sequence and functions as a switch, activating the expression of a coding sequence. If the coding sequence is activated, it is said to be transcribed. Transcription generally involves the synthesis of an RNA molecule (such as, for example, an mRNA) from a coding sequence. Promoters may be derived in their entirety from a native source, or be composed of different elements derived from different promoters found in nature, or even comprise synthetic nucleotide segments. It is understood by those skilled in the art that different promoters may direct the expression of a gene in different stages of development, or in response to different environmental conditions, or at various expression levels. Promoters which cause a gene to be expressed in most cell types at most times are commonly referred to as "constitutive promoters".

The term "operably linked" means that a selected nucleic acid sequence is in proximity with a promoter to allow the promoter to regulate expression of the selected nucleic acid sequence. In general, the promoter is located upstream of the selected nucleic acid sequence in terms of the direction of transcription.

As used herein, the term "homology" when used in relation to nucleic acid sequences refers to a degree of similarity or identity between at least two nucleotide sequences. There may be partial homology or complete homology (i.e., identity). "Sequence identity" refers to a measure of relatedness between two or more nucleotide sequences, expressed as a percentage with reference to the total comparison length. The identity calculation takes into account those nucleotide residues that are identical and in the same relative positions in their respective sequences. A gap, i.e. a position in an alignment where a residue is present in one sequence but not in the other is regards as a position with non-identical residues. A widely used and accepted computer program for performing sequence alignments is CLUSTALW v1.6 (Thompson, et al. Nucl. Acids Res., 22: 4673-4680, 1994).

The term "transgenic" when used in reference to an alga (i.e., a "transgenic alga") refers to an alga that contains at least one heterologous polynucleotide.

The term "antisense oligonucleotide" refers to an oligonucleotide that binds to target RNA by means of RNA-RNA or RNA-DNA or RNA-PNA (protein nucleic acid) interactions and alters the activity of the target RNA (for a review, see Stein and Cheng, 1993 Science 261, 1004-1012). Typically, antisense molecules are complementary to a target sequence along a single contiguous sequence of the antisense molecule. However, in certain embodiments, antisense oligonucleotide can be complementary to two (or even more) non-contiguous target sequences.

The term "expression", as used herein, refers to the production of a desired end-product molecule in a target cell. The end-product molecule may be, for example an RNA molecule.

As used herein, the term "transformation" refers to the transfer of molecules, such as, for example, nucleic acids, polynucleotide molecules, vectors, and the like into a target cell(s), and more specifically into the interior of a membrane-enclosed space of a target cell(s). The molecules can be "transformed" into the target cell(s) by any means known to those of skill in the art. Means of "transforming" molecules into a cell include, for example, but are not limited to: heat shock, calcium phosphate transfection, PEI transfection, electroporation, lipofection, gene bombardment, transfection reagent(s), viral-mediated transfer, and the like, or combinations thereof.

As used herein, the term "heterologous" when referred to RNAi molecule is directed to a recombinant DNA or RNA molecule which is introduced to and/or expressed within a target cell. The heterologous RNA molecule may be intact (that is, a full-length molecule) or may be cleaved within the cell at one or more cleavage sites.

As used herein, the term "target nucleic acid" refers to pre-mRNA and mRNA (or portions thereof).

As used herein, the term "heterologous" refers to gene or polynucleotide that originates outside of the organism of concern.

As used herein, the term "edible" refers to a compound or a composition suitable to be eaten as a food. In the context of the present invention, the term encompasses compounds/composition that can be eaten by insects and other plant and/or animal pests.

According to one aspect, the present invention provides a non-propagating transgenic microalga comprising at least one heterologous polynucleotide expressing RNAi molecule, wherein the RNAi molecule is targeted to a polynucleotide present within a xenogeneic organism.

According to certain embodiments, the RNAi molecule silences the expression of the polynucleotide present within the xenogeneic organism when the microalga is consumed by said organism. According to certain embodiments, the polynucleotide present within the xenogeneic organism is endogenous gene of said organism. According to other embodiments, the RNAi molecule is targeted to a gene or part thereof of a parasite or a pathogen of the xenogeneic organism.

According to certain embodiments, the RNAi molecule silences the expression of a polynucleotide present within a xenogeneic organism, wherein the xenogeneic organism is a pathogen of a host organism consuming the microalga.

According to additional embodiments, the RNAi molecule silences the expression of a polynucleotide present within a xenogeneic organism, wherein the xenogeneic organism is fed on a plant, particularly crop plant at least partially covered with the microalga.

According to certain embodiments, the RNAi molecule silences the expression of a polynucleotide present within a xenogeneic organism, wherein the xenogeneic organism is fed on an intervening organism consuming the microalga.

According to certain embodiments, the xenogeneic organism is a plant pest or parasite. According to certain exemplary embodiments, the plant pest is selected from the group presented in Table 1.

TABLE 1

| Plant pests | | | |
|---|---|---|---|
| Order | Family | Genus/Species | Affected Plants |
| Orthoptera | Acrididae | *Schistocerca gregaria* | Perl millet (*Pennisetum glaucum*), maize, sorghum, barley, rice, pasture grasses, sugarcane, cotton, fruit trees, date palms, banana plants, vegetables and weeds |

TABLE 1-continued

| Order | Family | Genus/Species | Affected Plants |
|---|---|---|---|
| | Acrididae | *locusta migratoria* | Perl millet (*Pennisetum glaucum*), maize, sorghum, barley, rice, pasture grasses, sugarcane, cotton, fruit trees, date palms, banana plants, vegetables and weeds |
| Lepidoptera | Noctuidae | *Spodoptera littoralis* | Cotton, Cabbage, Capsicum |
| | | *Helicoverpa zea* | Corn, Tomato, Lettuce, Broccoli |
| | | *Heliothis* (genus) | Tobacco, Cotton, Soybean, Pigeon Pea |
| | Geometridae | *Trichoplusia ni* | *Brassicaceae* crops including Cabbage, Tomato, Cucumber, Collard Greens, Potato |
| | | *Ascotis/ selenaria* | Alfalfa, Citrus, Coffee, Mulberry, Peanuts, Tea, Avocado |
| | Plutellidae | *Plutella/ xylostella* | Cabbage, Radish, Horseradish |
| | Gelechiidae | *Pectinophora gossypiella* | Cotton |
| | | *Scrobipalpa ocellatella* | Beet |
| | | *Phthorimaea operculella* | Potatoes, Tobacco |
| | Castniidae | *Paysandisia archon* | Palm |
| | Crambidae | *Duponchelia fovealis* | Corn, Cucumbers, Peppers, Pomegranate, Tomatoes, certain herbs and flowers as Anemone, Begonia, Cyclamen etc |
| | Gracillariidae | *Phyllonorycter blancardella Phyllonorycter crataegella* | Apples |
| | Tortricidae | *cacoecimorpha pronubana* | Olive trees and Avocado |
| | | *Argyrotaenia ljungiana* | Vines, Maize and fruit trees |
| | Tineidae | *Opogona sacchari* | Banana, Pineapple, Corn |
| Coleoptera | Elateridae | *Agriotes sputator* | Leaves but mostly roots of Cereals, Maize, Sunflower, Sugar Beet, Potato and Peanut |
| | | *Agriotes lineatus* | |
| | Capnodis | *Capnodis carbonaria* | Almond, Apricot, Cherry (*Prunus Vulgaris Linnaeus*), Nectarine, Peach, Plum |
| | Chrysomelidae | *Leptinotarsa decemlineata* | Potatoes, Tomatoes, Eggplants |
| | | *Oulema melanopus* | |
| | | *Phyllotreta cruciferae* | Canola, *Brassicaceae* crops including Radish and Cabbage |
| | | *Phyllotreta striolata* | Canola, *Brassicaceae* crops including Radish and Cabbage |
| | Scarabaeidae | *Maladera insanabilis* | Sweet potatoes |
| | Curculionidae | *Rhynchophorus ferrugineus* | Palm |
| | | *Sitophilus zeamais* | Maize, Wheat, Rice, Sorghum, Oats, Barley, Rye, Buckwheat, Peas |

According to certain embodiments, the xenogeneic organism is an animal pest or parasite. According to certain exemplary embodiments, the animal is fish, and the pest or parasite is selected from the group presented in Table 2.

TABLE 2

Fish pests

| Family | Known species | Affected animals |
|---|---|---|
| Insects: | | |
| Lernaeidae | Lernaea cyprinacea | Freshwater fish as Cyprinids and Salmonids |
| Caligidae | Lepeophtheirus salmonis | Farmed and wild Atlantic salmon |
| | Caligus elongatus | Farmed and wild Atlantic salmon |
| Pennellidae | Lernaeocera branchialis | Cod or other fishes of the cod family |
| | Lernaeocera lusci | Cod and sole fish |
| Lernaeopodidae | Salmincola californiensis | Farmed salmonids |
| | Sphyrion lumpi | Redfish |
| Argulidae | Argulus foliaceus | Freshwater fish as carps, salmonids, |
| | Argulus japonicus | Freshwater fish mainly common car and goldfish |
| Cymothoidae | Ceratothoa gaudichaudii and Ceratothoa cf. imbricata | Salmon farms in Chile and Australia |
| Worms: | | |
| Gyrodactylidae | Gyrodactylus salaris | Salmonids and particularly Atlantic salmon |
| | Gyrodactylus salmonis | Salmonids |
| | Gyrodactylus anguillae | Freshwater fish as eels |
| Troglotrematidae | Nanophyetus salmincola | Salmonids |
| Dactylogyridae | Dactylogyrus vastator | Freshwater fish as Common carp and goldfish |
| | Dactylogyrus extensus | Freshwater fish as Common carp and goldfish |
| | Dactylogyrus minutus | Freshwater fish as Common carp |
| Heterophyidae | Centrocestus formosanus | Freshwater fish |
| | Haplorchis pumilio | Freshwater fish |
| Clinosomatidae | Clinostomum marginatum | Freshwater fish |
| Camallanidae | Camallanus cooked | Aquarium fish |
| Capillariidae | Capillaria | Aquarium fish |
| Bothriocephalidae | Bothriocephalus acheilognathi | Freshwater fish as Cyprinidae |
| Lernaeidae | Lernaea | Aquarium fish as goldfish and koi |
| Tetraonchidae | Tetraonchus awakurai | Masou salmon |
| | Tetraonchus oncorhynchi | Masou salmon |
| Diplectanidae | Diplectanum aequans | Sea bass |
| | Diplectanum laubieri | Sea bass |
| Capsalidae | Neobenedenia melleni | Marine teleost species |
| Diphyllobothriidae | Diphyllobothrium dendriticum | Salmonids |
| Philometridae | Hysterothylacium bidentatum | Sterlet |

According to certain additional exemplary embodiments, the animal is a domestic animal, and the xenogeneic organism is pest or a parasite selected from the group presented in Table 3.

TABLE 3

Pests of domestic animals

| Family | Known species | Affected animals |
|---|---|---|
| Insects: | | |
| Haematopinidae | Haematopinus eurysternus | Cattle |
| | Haematopinus suis | Swine |
| Trichodectiidae | Bovicola bovis | |
| | Bovicola ovis | Sheep |
| | Damalinia limbata | Goat |
| Menoponidae | Menacanthus stramineus | Chickens |
| | Menopon gallinae | Chickens |
| Pulicidae | Echidnophaga gallinacea | Chickens |
| Worms: | | |
| Fasciolidae | Fasciola hepatica | Sheep and cattle |
| | Fascioloides magna | Domestic ruminants |
| Dicrocoeliidae | Dicrocoelium dendriticum | Cattle |
| Paramphistomatidae | Paramphistomum cervi | Cattle and sheep |
| | Calicophoron daubneyi | Cattle and sheep |
| Taeniidae | Taenia saginata | Cattle and human |
| | taenia solium | Pigs and human |
| Anoplocephalidae | Moniezia expansa | Sheep, goats and cattle |
| | moniezia benedini | Sheep, goats and cattle |
| | thysanosoma actinoides | Sheep, goats |
| Trichostrongylidae | Trichostrongylus axei | horse, cattle, sheep, goat |
| Trichostrongylidae | Teladorsagia circumcincta | Sheep and goats |
| | Ostertagia ostertagi | Cattle |
| | Haemonchus contortus | Sheep and goats |
| | mecistocirrus digitatus | Cattle, sheeps, goat, pigs |
| Strongylidae | Strongylus vulgaris | Horse |
| | Oesophagostomum bifurcum | Goats, pigs |
| stephanuridae | stephanurus dentatus | Pigs |
| Ascarididae | Ascaris suum | Pigs |
| Trichinella | Trichinella spiralis | Pigs, horses |

According to certain embodiments, the RNAi molecule comprises a sense strand and an antisense strand, the sense strand and the antisense strand together form a duplex, said sense strand comprises at least 19 contiguous nucleic acids having at least 90% identity to the target polynucleotide present within a xenogeneic target organism.

According to certain embodiments, the RNAi molecule is targeted to a polynucleotide of an insect. According to certain exemplary embodiments, the RNAi molecule is targeted to the clk gene. According to some embodiments, the clk gene comprises the nucleic acid sequence set forth in SEQ ID NO:1 (GenBank: HQ428033.2).

According to these embodiments, the RNAi molecule comprises a sense strand comprising a polynucleotide sequence having at least 90% homology, typically at least 95% homology, more typically at least 99% homology to the nucleic acids sequence set forth in SEQ ID NO:1 or a fragment thereof, and an antisense strand comprising a polynucleotide having at least 90% homology, typically at least 95% homology, more typically at least 99% homology to a nucleic acids sequence complementary to SEQ ID NO:1 or a fragment thereof.

According to certain exemplary embodiments, the RNAi molecule comprises a sense strand comprising the polynucleotide sequence set forth in SEQ ID NO:2 and an antisense strand comprising the polynucleotide sequence set forth in SEQ ID NO:3.

SEQ ID NO:1 encodes for the clock gene (clk) of desert locust. It was shown that treatment with double-stranded RNA targeted to clk is lethal in adults and fifth instar nymphs of the desert locust, *Schistocerca gregaria* (Tobbacka et al. 2011. Insect Biochemistry and Molecular Biology 41:313-321). The present invention provides a method for feeding the desert locust or the migratory locust (*Locusta migratoria*) with RNAi molecules produced by microalgae. The non-propagating microalgae of the invention are applied onto wheat sprouts, seedlings or mature plants which are later consumed by the locust. According to certain exemplary embodiments, the non-viable microalgae or a composition comprising same are sprayed on plants consumed by the locust.

According to certain embodiments, the RNAi molecule is targeted to a polynucleotide of a copepod. According to certain exemplary embodiments, the copepod is *Lepeophtheirus salmonis* and the RNAi molecule is targeted to the *Lepeophtheirus salmonis* COPB2 gene. According to these embodiments, the RNAi molecule comprises a sense strand comprising a polynucleotide sequence having at least 90% homology, typically at least 95% homology, more typically at least 99% homology to the nucleic acids sequence set forth in SEQ ID NO:35 or a fragment thereof, and an antisense strand comprising a polynucleotide having at least 90% homology, typically at least 95% homology, more typically at least 99% homology to a nucleic acids sequence set forth in SEQ ID NO:36 or a fragment thereof.

According to other embodiments, the RNAi has a beneficial effect on at least one of the growth, development and survival of the consuming animal. Each possibility represents a separate embodiment of the present invention.

According to other embodiments, the RNAi has a therapeutic effect on the animal consuming the transgenic microalgae. According to certain embodiments, the RNAi provides resistance to a land pest. According to certain embodiments, the RNAi provides resistance to an aquatic pest According to certain embodiments, the RNAi provides resistance to a virus.

According to certain embodiments, the organism is a fish. The fish may optionally be grown for food or for a non-food purpose (the latter including but not limited to ornamental and the like).

According to certain embodiments, the organism is a crustacean. The crustacean may optionally be grown for food or for a non-food purpose (the latter including but not limited to ornamental and the like).

According to another embodiment, the organism is a poultry animal. Poultry are typically grown in large numbers therefore an advantageous means of providing them a biologically active agent is by oral delivery.

According to certain embodiments, the non-propagating transgenic microalgae of the present invention can be administered per se, or can be formulated into an edible composition further comprising edible diluents, excipients or carriers. According to certain exemplary embodiments, the non-propagating transgenic microalgae are dried, when administered alone as well when administered within a composition.

Drying the transgenic microalgae of the present invention requires the use of drying techniques which are suitable for preserving the function of the RNAi activity once the microalgae is consumed by the xenogeneic organism. Typically, the entire drying process is performed at a temperature below 50° C.

According to certain exemplary embodiments, the transgenic microalgae are freeze-dried. According to other embodiments, the transgenic microalgae are dried using microwave vacuum drying techniques. Both methods are designed for high-volume, low-temperature dehydration of solid, liquid, granular or encapsulated material.

According to certain exemplary embodiments, the dried transgenic microalgae are mixed with at least one edible diluent, excipient or carrier.

According to certain exemplary embodiments, the dried transgenic microalgae are mixed with gelatin. According to additional exemplary embodiments, the dried transgenic microalgae are mixed with fish oil. According to some embodiments, the gelatin or fish oil is added at an amount of 0.1-10%, typically 0.5-5% w/w.

The microalgae or the composition comprising same can be further used as food additive. According to certain embodiments, the algae-based edible composition is an animal food composition.

According to yet other embodiments, the algae-based edible composition serves as a food source for insect either alone or in combination with the natural food of the insect. According to certain exemplary embodiments, the edible composition serves as a food source for insects of the order selected from, but not limited to, the group consisting of Lepidoptera, Coleoptera and Orthoptera. According to other exemplified embodiments, the algae-based edible composition is a food source for desert locust (*Schistocerca gregaria*). According to yet other embodiments, the algae-based edible composition is a food source for migratory locust (*Locusta migratoria*). According to yet other embodiments, the algae-based edible composition is a food source for *Spodoptera littoralis* According to yet other embodiments, the algae-based edible composition is a food source for nematode. According to yet other embodiments, the algae-based edible formulation is a food source for the host of sea lice. According to yet other embodiments, the algae-based edible composition is for feeding fish. According to yet other embodiments, the algae-based edible formulation is a food source for crustaceans. According to certain exemplary embodiments, the fish and/or crustaceans are infected with a virus. According to these embodiments, the RNAi molecule within the transgenic molecule is targeted to silence a viral gene. According to yet other embodiments, the algae-based edible composition is for feeding poultry. According to certain embodiments, the edible composition may further comprise additional active therapeutic and/or nutritional agents.

The algae-based edible composition of the invention may also be admixed, encapsulated, or associated with other molecules, or mixtures of compounds, or attractants as for example liposomes, pheromones for assisting in uptake, distribution and/or a absorption.

Composition and formulation for oral administration include powders, granules, microparticulates, suspensions or solutions in water or non-aqueous media, capsules, gel capsules, sachets, tablets, or minitablets.

Composition and formulation suitable for applying the algae-based edible composition on plants and/or animals include powders, granules, microparticulates, suspensions or solutions in water or non-aqueous media such as gelatin or oil.

Various microalgae species can be used according to the teachings of the present invention as long as the microalgae maintain or regenerate their cell wall structure after transformation. According to certain embodiments, the microalga used according to the teachings of the present invention is a marine microalga. According to certain embodiments, the microalga is selected from the group consisting of, but not restricted to, *Phaeodactylum tricornutum; Dunaliella* spp.; *Nannochloropsis* spp. including *Nannochloropsis oculata,*

*Nannochloropsis sauna, Nannochloropsis gaditana; Nannochloris* spp., *Tetraselmis* spp. Including *Tetraselmis suecica, Tetraselmis chuii; Isochrysis galbana; Pavlova* spp.; *Amphiprora hyaline; Chaetoceros muelleri;* and *Neochloris oleoabundans*. Each possibility represents a separate embodiment of the present invention.

According to certain specific embodiments, the microalga is selected from the group consisting of *Phaeodactylum tricornutum, Nannochloris* spp., *Nannochloropsis* spp. and *Dunaliella* spp. Each possibility represents a separate embodiment of the present invention.

According to other specific embodiments, the microalga is *Phaeodactylum tricornutum*.

According to certain embodiments, the target gene expression is being inhibited by at least 10%, 30%, 50%, 70%, 90%, typically 99% when compared to same target gene once an organism is not consuming said transgenic microalga.

According to an additional aspect, the present invention provides a method for oral delivery of RNAi molecule to an organism, the method comprising orally administering to the organism a non-propagating transgenic microalga comprising at least one heterologous RNAi molecule, wherein the RNAi molecule is targeted to a polynucleotide present within said organism thereby inhibiting its expression.

According to some embodiments, the non-propagating transgenic eukaryotic microalgae are administered within an animal food composition. The composition is formulated by any means as described hereinabove. The composition is formulated for feeding any of the organisms as described hereinabove.

According to yet additional embodiments, the non-propagating transgenic eukaryotic microalgae are administered with the natural food of the organism. According to these embodiments, the microalgae coat, at least partially, the natural food of the organism. The microalgae can be formulated to coat the organism natural food as is known in the art and as described hereinabove.

Any method for transforming microalgae as is known in the art can be used according to the teachings of the present invention. Transformation methods include particle bombardment, electroporation, microporation, vortexing cells in the presence of heterologous DNA, acid washed beads and polyethylene glycol-mediated transformation. Methods and tools for transformation of eukaryotic algae can be found, for example, in International (PCT) Application Publication No. WO 1997/039106.

Typically, to prepare vectors for making the transgenic algae, the polynucleotide transcribing the RNAi is first cloned into an expression vector, a plasmid that can integrate into the algal genome. In such an expression vector, the DNA sequence which encodes the heterologous RNAi is operatively linked to an expression control sequence, i.e., a promoter, which directs RNA synthesis. The promoter can be an endogenous promoter, i.e., a promoter that directs transcription of genes that are normally present in the algae. According to certain embodiments, the vector further comprises a polynucleotide encoding a resistance gene to enable selection of transformed algae. According to certain currently exemplary embodiments, the vector comprises a polynucleotide encoding a protein conferring resistance to zeocine and phleomycin.

Culturing conditions of the transformed algae depend on the alga species used, as is known to the skilled Artisan and as exemplified herein below. Typically, the algae are grown under conditions that enable photosynthesis. Since photosynthesis requires sunlight and $CO_2$ and the microalgae further require either fresh, brackish or marine water mixed with the appropriate fertilizers to grow, microalgae can be cultivated in, for example, open ponds and lakes. However, the open systems are more vulnerable to contamination than a closed system, and furthermore, genetically modified microalgae grown in open aqueous reservoirs may be taken as hazardous to the environments. In addition, in open systems there is less control over water temperature, $CO_2$ concentration, and lighting conditions. The growing season is largely dependent on location and, aside from tropical areas, is limited to the warmer months of the year. An open system, however, is cheaper to set up and/or maintain than a closed system.

Another approach to growing the microalgae is thus to use a semi-closed system, such as covering the pond or pool with a structure, for example, a "greenhouse-type" structure. While this can result in a smaller system, it addresses many of the problems associated with an open system. The advantages of a semi-closed system are that it can allow for the desired microalgae to be dominant over an invading organism by allowing the microalgae of interest to out-compete the invading organism for nutrients required for its growth, and it can extend the growing season. For example, if the system is heated or cooled, the microalgae can grow year round.

Alternatively, the microalgae can be grown in closed structures such as photobioreactors, where the environment is under stricter control than in open systems or semiclosed systems. A photobioreactor is a bioreactor which incorporates some type of light source to provide photonic energy input into the reactor. The term photobioreactor can refer to a system closed to the environment and having no direct exchange of gases and contaminants with the environment. A photobioreactor can be described as an enclosed, illuminated culture vessel designed for controlled biomass production of phototrophic liquid cell suspension cultures. Examples of photobioreactors include, for example, glass containers, plastic/glass tubes, tanks, plastic sleeves, and bags. Examples of light sources that can be used to provide the energy required to sustain photosynthesis include, for example, fluorescent bulbs, LEDs, and natural sunlight. Because these systems are closed everything that the organism needs to grow (for example, carbon dioxide, nutrients, water, and light) must be introduced into the bioreactor. Photobioreactors, despite the costs to set up and maintain them, have several advantages over open systems, they can, for example, prevent or minimize contamination, offer better control over the culture conditions (for example, pH, light, carbon dioxide, and temperature), prevent water evaporation, lower carbon dioxide losses due to degassing, and permit higher cell concentrations. On the other hand, certain requirements of photobioreactors, such as cooling, mixing, control of oxygen accumulation and bio-fouling, make these systems more expensive to build and operate than open systems or semi-closed systems. Photobioreactors can be set up to be continually harvested (as is with the majority of the larger volume cultivation systems), or harvested one batch at a time (for example, as with polyethlyene bag cultivation). A batch photobioreactor is set up with, for example, nutrients, microalgae, and water, and the microalgae is allowed to grow until the batch is harvested. A continuous photobioreactor can be harvested, for example, either continually, daily, or at fixed time intervals.

$CO_2$ can be delivered to any of the systems described herein, for example, by bubbling in $CO_2$ from under the surface of the liquid containing the microalgae. Also, spargers can be used to inject $CO_2$ into the liquid. Spargers are, for example, porous disc or tube assemblies that are also referred to as Bubblers, Carbonators, Aerators, Porous Stones and Diffusers.

Nutrients that can be used in the systems described herein include, for example, nitrogen (in the form of $NO_3^-$ or $NH_4$), phosphorus, and trace metals (Fe, Mg, K, Ca, Co, Cu, Mn, Mo, Zn, V, and B). The nutrients can come, for example, in a solid form or in a liquid form. If the nutrients are in a solid form they can be mixed with, for example, fresh or salt water prior to being delivered to the liquid containing the microalgae, or prior to being delivered to a photobioreactor.

The microalgae can be grown in large scale cultures, where large scale cultures refers to growth of cultures in volumes of greater than about 5 liters, or greater than about 10 liters, or greater than about 90 liters. Large scale growth can also be growth of cultures in volumes of 300 liters or more, 1000 liters or more, or 5000 liters and up.

Optimal growth temperature is typically about 18° C. to about 25° C., however it is species dependent. According to certain embodiments microalgae cell reach a density of $10^5$ to $10^8$/ml before harvesting.

Post-harvest processing of some sort may be used to prepare the material for oral consumption or as a food composition. Conventional processes typically include at least partial separation of the algal biomass from the liquid culture in which the algae were grown. Optionally, the algal biomass can be homogenized and/or dried to form pellets of various sizes, depending on the target subject and mode of application. Other modes of preparation include spray drying, fluid bed drying, or even providing the material as a liquid suspension.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods
Algae Culturing and Harvesting

Algae culturing and harvesting was done as described in U.S. Patent Application Publication No. 2011/0081706 to the Applicant of the present invention. Briefly, algae (*Phaeodactylum tricornutum*) were cultured in filtered sea water enriched with F/2 nutrient for growing diatoms (modified from Andersen R et al. 2005. Recipes for freshwater and seawater media. In: Algal Culturing Techniques (R. A. Andersen, Eds), pp. 429-538. Elsevier, Amsterdam). F/2 was added every 72 h at a dosage of 1:1000 to the final culture volume. A constant temperature regime was maintained at 21° C. Light: dark was set at 16:8 hours at a light intensity of 100 µmol photons per $m^2 s^1$. $CO_2$ was mixed with air and delivered to the cultures at controlled ratio via the aeration systems. Algae were harvested for experiment near their maximal culture densities. To help flocculation of the algae calcium hydroxide was added to the culture as a fine suspension of particles in water containing 0.15 g/ml $Ca(OH)_2$, and the culture was then filtered or centrifuged. The resulting algae sediment was lyophilized to form algae powder. The algae powder was kept in vacuum bag at a temperature of 2-8° C.

Algae Transformation
I. Transformation by Particle Bombardment

Fresh algal culture were grown to mid exponential phase ($2-5 \times 10^6$ cells/ml) in artificial sea water (ASW) F/2 media as described above. 24 hours prior to bombardment cells were harvested, washed twice with fresh ASW+F/2 and resuspended in 1/10 of the original cell volume in ASW+F/2. 0.5 ml of the cell suspension was spotted onto the center of a 55 mm Petri dish containing solidified ASW+F/2 media. Plates were left to dry under normal growth conditions. Bombardment was carried out using a PDS 1000/He biolistic transformation system according to the manufacturer's instructions (BioRad Laboratories Inc., Hercules, Calif. USA) using M17 tungsten powder (BioRad Laboratories Inc.) for cells larger than 2 microns in diameter, and tungsten powder comprised of particles smaller than 0.6 microns (FW06, Canada Fujian Jinxin Powder Metallurgy Co., Markham, ON, Canada) for smaller cells. The tungsten was coated with linear DNA. 1100 or 1350 psi rupture discs were used. All disposables were purchased from BioRad Laboratories Inc. After bombardment the plates were incubated under normal growth conditions for 24 hours after which the cells were plated onto selective solid media and incubated under normal growth conditions until single colonies appeared.

II. Transformation by Microporation

A fresh algal culture was grown to mid exponential phase in ASW+F/2 media as described above. A 10 ml sample of the culture was harvested, washed twice with Dulbecco's phosphate buffered saline (DPBS, Gibco, Invitrogen, Carslbad, Calif., USA) and resuspended in 250 µl of buffer R (supplied by Digital Bio, NanoEnTek Inc., Seoul, Korea, the producer of the microporation apparatus and kit). After adding 8 µg linear DNA to every 100 µl cells, the cells were pulsed. A variety of pulses is typically needed, depending on the type of cells, ranging from 700 to 1700 volts, 10-40 msec pulse length; each sample was pulsed 1-5 times. Immediately after pulsing, the cells were transferred to 200 µl fresh culture media (non-selective). After incubating for 24 hours in low light at 25° C., the cells were plated onto selective solid media and incubated under normal culture conditions until single colonies appeared.

Hemolymph Collection

Animals (of the species described herein below) were washed in water and hemolymph of a pool of 8-10 animals was collected into an eppendorf tube. Samples were centrifuged at 14000 g, 4° C. for 5 minutes and transferred into a new Eppendorf tube containing Trizol (Ambion life technologies; Cat #15596026). Samples were put into liquid nitrogen and kept frozen until use.

RNA Purification

RNA extraction from algae was performed using Master Pure Plant RNA kit (Epicentre; cat #MPRO9100), according to the manufacturer's instructions. The samples were resuspended in RNAse-free water and incubated with TURBO DNA free kit (Ambion cat #AM1907), according to the manufacturer's instructions.

RNA extraction from insects hemolymph was performed using either Trizol (Ambion life technologies; Cat #15596026) or by miRNeasy Serum/Plasma Kit (QIAGEN Cat #217184) according to the manufacturer's instructions.

RNA extraction from insects' organs was performed using Trizol (Ambion life technologies; Cat #15596026). The RNA was incubated with TURBO DNA free kit (Ambion cat #AM1907), according to the manufacturer's instructions.

cDNA Synthesis

1 µg of total RNA was used as a template for cDNA synthesis using SuperScriptII Reverse Transcriptase (Invitrogen; cat #100004925) supplemented with Random Hexamer primers (Fermentas; cat #S0142) or using iScript™ cDNA Synthesis Kit (Bio-Rad; cat #170-8890) according to the manufacturer's instructions.

qRT-PCR Analysis

Analysis of cDNA was performed by qRT-PCR relative quantification using Biorad CFX96 with Platinum SYBR green (Invitrogen; cat #11744500) according to the manufacturer's instructions. dsRNA targeted to Green Fluorescent Protein (GFP) encoding mRNA was amplified using ds-GFP Q2 For junc and ds-GFP Q2 Rev linker primers (Table 1). TBP (encoding TATA box binding protein) was used as a reference gene and was amplified with Q-TBP-fw and Q-TBP-ry (Table 1). dsRNA targeted to the red fluorescent protein mCherry was amplified using ds-mCherry Q1 For 5' and ds-mCherry Q1 Rev junc (Table 1). Internal control (Primerdesign, UK; Cat #INT-RNA-FAM) was used as reference. Data analysis was performed according to the ΔΔCt method (Livak et al., 2001. Methods 25:402-408).

Analysis of the expression levels of the clock (clk) gene was performed using Sg_clk_F and Sg_clk_R primers, designated to amplify *Schistocerca gregaria* clock mRNA sequence. The primers dsCLOCK Q4 fw and dsCLOCK rev were designed to specifically amplify the clock dsRNA sequence that was transformed and expressed in the algae (Table 4). Quantification of timeless and period genes was performed using the Sg_tim_F and Sg_tim_R and Sgper_F and Sgper_R, respectively (Table 4). Beta actin or GAPDH were used as reference genes and were amplified with Sg_b_actin_F and Sg_b_actin_R and Sg_GAPDH_F and Sg_GAPDH_R, respectively (Table 4). Data Analysis was performed according to the ΔΔCt method and by separation of the qRT-PCR products on agarose gel.

TABLE 4

List of primers

| Primer name | Primer sequence | SEQ ID NO. |
|---|---|---|
| Q-TBP-fw | ACCGGAGTCAAGAGCACACAC | 7 |
| Q-TBP-rv | CGGAATGCGCGTATACCAGT | 8 |
| ds-GFP Q2 For junc | GCAGCTCGCCGGTACCTA | 9 |
| ds-GFP Q2 Rev linker | TTGTTTCCGACGGCACACT | 10 |
| ds-mCherry Q1 For 5' | CCGTCATGCAGAAAAAGACCAT | 11 |
| ds-mCherry Q1 Rev junc | CTGCGTAGGTACCCTGCTTGA | 12 |
| dsCLOCK Q4 fw | GGACATTCTCCCTCACAAAACAA | 13 |
| dsCLOCK Q4 rev | CAAATGCGATACCAACCTCAAC | 14 |
| Sg_GAPDH_F | GTCTGATGACAACAGTGCAT | 15 |
| Sg_GAPDH_R | GTCCATCACGCCACAACTTTC | 16 |
| Sg_b_actin_F | AATTACCATTGGTAACGAGCGATT | 17 |
| Sg_b_actin_R | TGCTTCCATACCCAGGAATGA | 18 |
| Sg_tim_F | TTGGAATTGGAGTTGGAACATGT | 19 |
| Sg_tim_R | AGTCTACCAATGGATGGTTTGACA | 20 |
| Sg_per_F | ACCAGATCGGAGCCAGCTT | 21 |
| Sg_per_R | CTTCTGGATGTTGTCGTTGTAGTT | 22 |

TABLE 4-continued

List of primers

| Primer name | Primer sequence | SEQ ID NO. |
|---|---|---|
| Sg_clk_F | CCATGAAGCTTTGATGCAGAAG | 23 |
| Sg_clk_R | CTGGCTTTGAGTTCCATTGATG | 24 |

Example 1: Expression of clk, GFP and mCherry dsRNA in Algae

Construction of dsRNA Targeted to clk mRNA of *Schistocerca gregaria*

The sense (SEQ ID NO:2) and antisense (SEQ ID NO:3) fragments of the clk gene were synthesized by Biomatik USA. The sense fragment was cloned by BamHI, SacII and the antisense fragment was cloned by SacI, KpnI. The clk fragments were cloned in the sense and antisense orientations into an intron contained pPhaT-cassette (FIG. 1, the pPhat cassette having the nucleic acid sequence set forth in SEQ ID NO:37).

Construction of dsRNA Targeted to GFP and mCherry mRNA:

GFP sense strand (SEQ ID NO:4) was amplified by PCR with the following oligonucleotides: BamHI Sense GFP F 5'-GGGATCCATGGTGAGCAAGGGC GAGG-3' (SEQ ID NO:25). SacII Sense GFP R 5'-GCCGCGGGGCGAGCTGCACGCTGCC-3' (SEQ ID NO:26). GFP antisense strand (SEQ ID NO:5) was amplified by PCR with the following oligonucleotides: SacI Antisense GFP F 5'-GGAGCTCATGGTGA GCAAGGGCGAGG-3' (SEQ ID NO:27). KpnI Antisense GFP R 5'-GGGTACCG GCGAGCTGCACGCTGCC-3' (SEQ ID NO: 28).

mCherry sense strand (SEQ ID NO:29) was amplified by PCR with the following oligonucleotides: BamHI Sense mCherry F 5'-GGGATCCATGGTAAGTAAGGGGGAGG-3' (SEQ ID NO:30) and SacII Sense mCherry R: 5'-GCCGCGGCTGCTTGATTTCGCCCTTG-3' (SEQ ID NO:31). For the amplification of the mCherry antisense strand (SEQ ID NO:32) the following primers were used: SacI Antisense mCherry F: 5'-GGAGCT-CATGGTAAGTAAGGGGGAGG-3' (SEQ ID NO:33). KpnI Antisense mCherry R 5'-GGGTACCCTGCTTGAT-TTCGCCCTTG-3' (SEQ ID NO:34).

Figure 2:
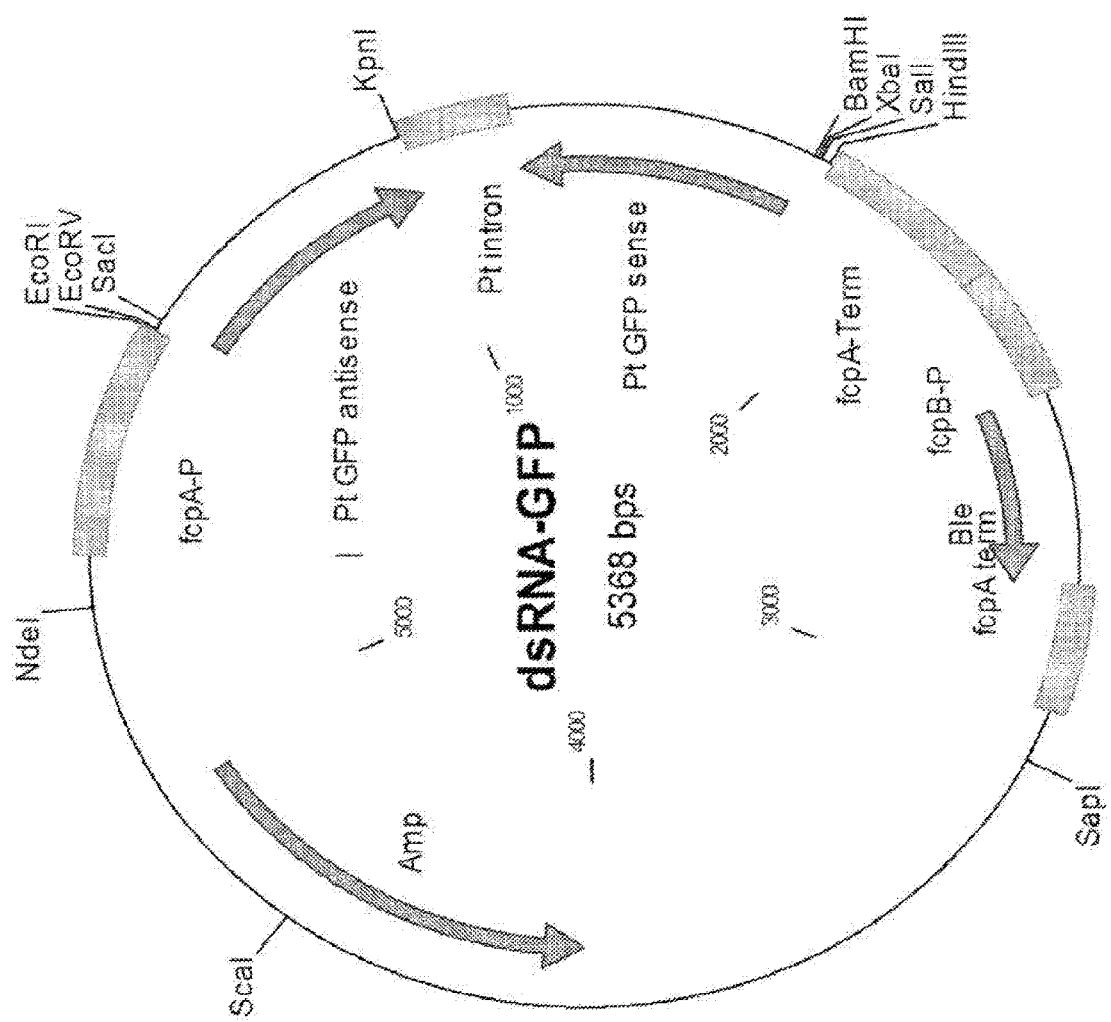
Figure 3:
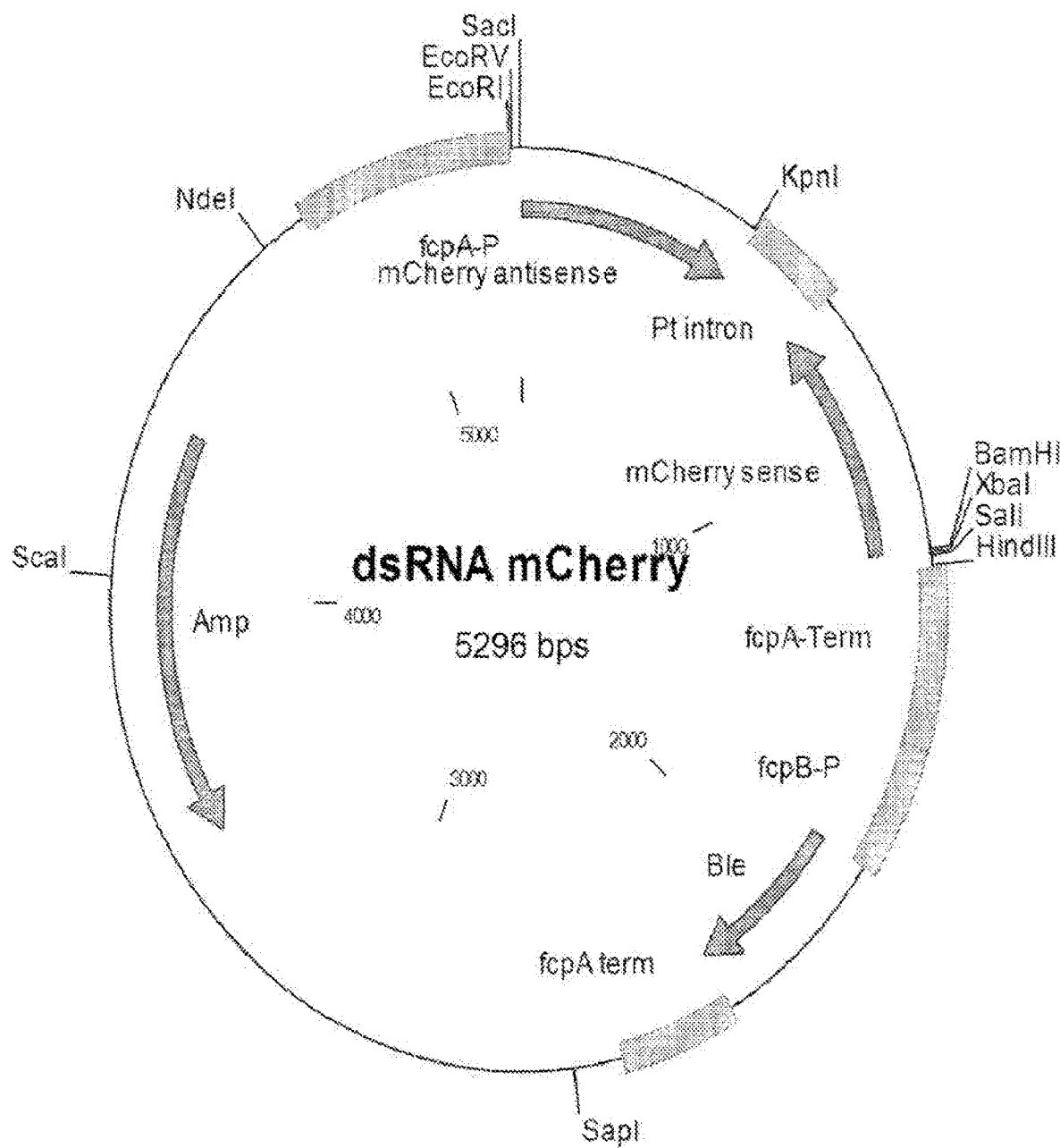

Constructs of clk, and mCherry dsRNA were prepared in pPhaT under the fcpA constitutive promoter and a construct of GFP was prepared in pPhaT under the inducible promoter ptCAI (FIG. 2 and FIG. 3, respectively). The constructs were transformed into the algae (*P. tricornutum*) by particle bombardments as described hereinabove. After transformation, algae were transferred to selection plates containing Zeocin (Invivogen; Cat #ant-zn-1; 100 μg/ml). Positive clones of algae expressing dsRNA targeted to clk (dsRNA-clock or dsclock), to GFP (dsRNA-GFP or dsGFP) and to mCherry (dsRNA-mCherry or dsmCherry) were cultivated and algae were grown for the animal feeding trials.

Example 2: Delivery by Feeding of an Intact dsRNA to the Mealworm Beetle Hemolymph Larvae of mealworm beetle, *Tenebrio molitor*, were placed in cultivation chambers, with 12 h/12 h light/dark illumination regime at constant temperature of 24° C. and relative humidity of 50%. Leaves of cabbage were brushed with powder of transgenic algae expressing the dsRNA targeted to mCherry (dsRNA-mCherry or dsmCherry) or with powder of wild type algae such that all the leaves were homogenously covered with the alga powder. To enable good application of the algae powder onto the plant material algae powder (of wild type as well as of transformed algae) was mixed with 5% gelatin in artificial sea water (ASW) diluted 1:3 with double-distilled water (DDW). The *Tenebrio molitor* larvae were deprived of food for 16 hours. At the day of the experiment the larvae were fed with the algae-brushed cabbage leaves or with leaves covered only with gelatin (mock) for 3 to 5 hours. Thereafter hemolymph was collected and samples were flash-frozen and stored at −80° C. until RNA extraction.

Figure 4:
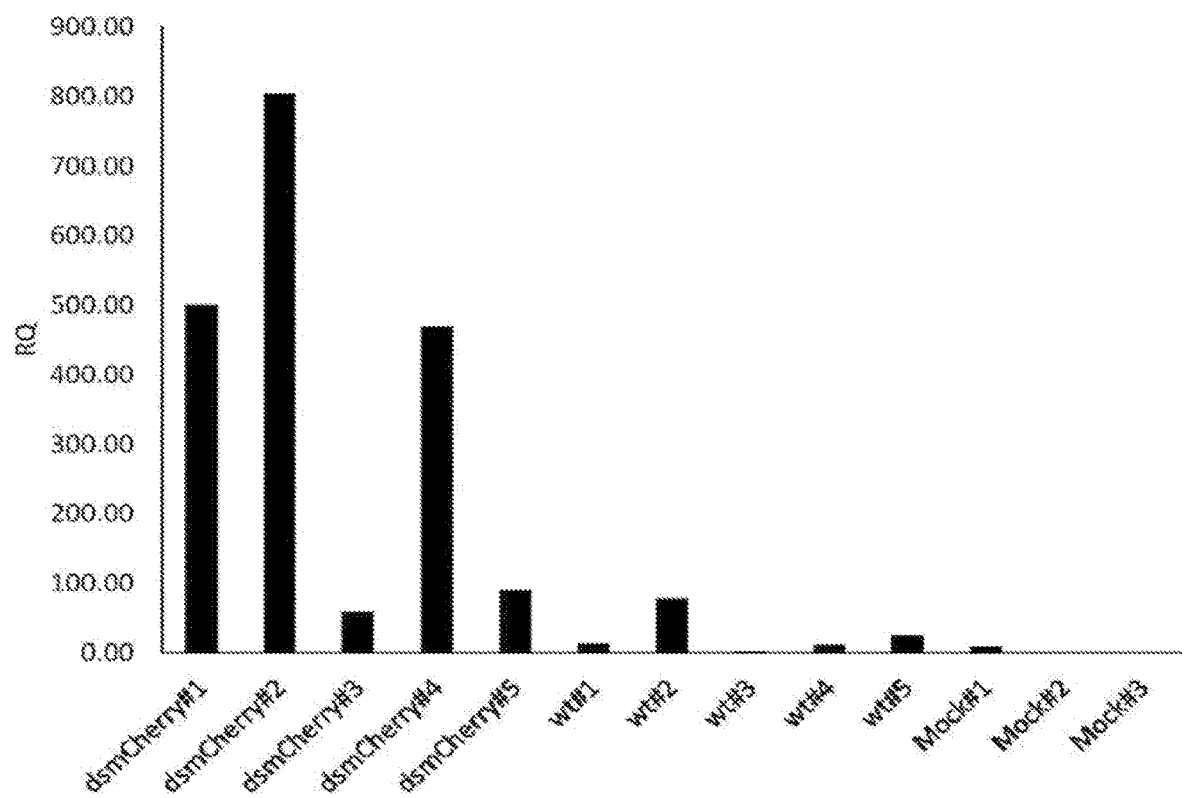
Figure 5:
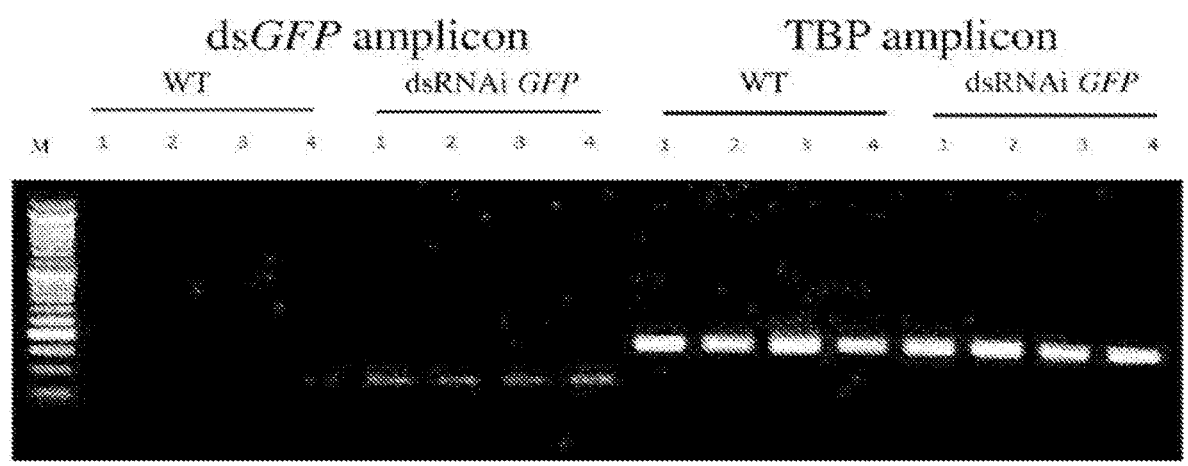
Figure 6A:
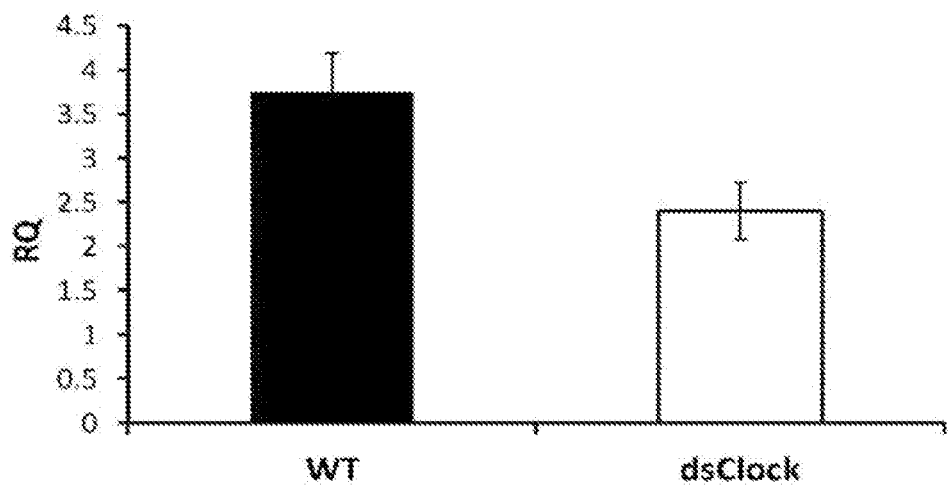
Figure 6B:
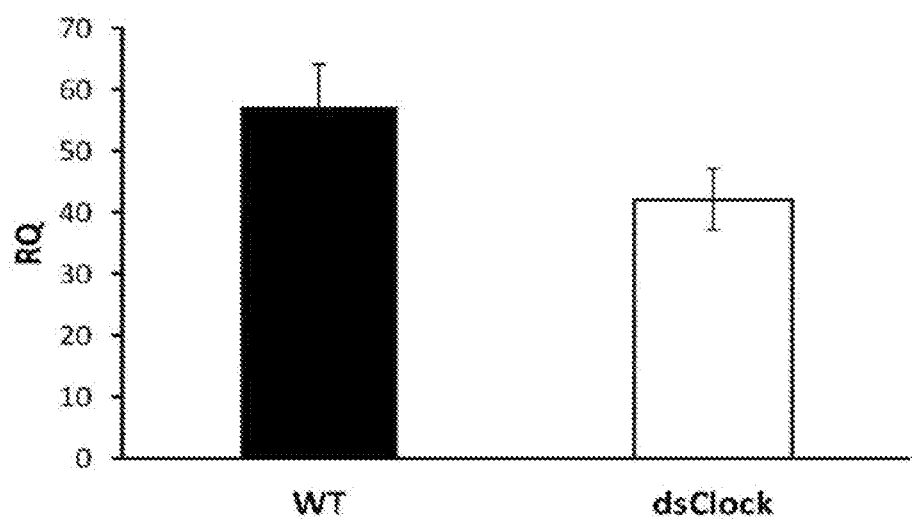

RNA extracted from the hemolymph samples was subjected to relative quantification by qRT-PCR analysis with primers specific to dsmCherry. Synthetic RNA (Primer Design) was used as a reference. Analysis was performed using the ΔΔCt method. Over 20 fold increase in dsmCherry RNA levels was demonstrated in 3 out of the 5 samples obtained from animals fed with dsmCherry expressing algae, compared to animals fed with WT algae. Each sample contained a pool of hemolymph from 5 animals (FIG. 4).

The results presented herein demonstrate for the first time the ability to deliver dsRNA molecules to the hemolymph of mealworm beetle by feeding larvae with algae expressing the dsRNA.

Figure 7A:
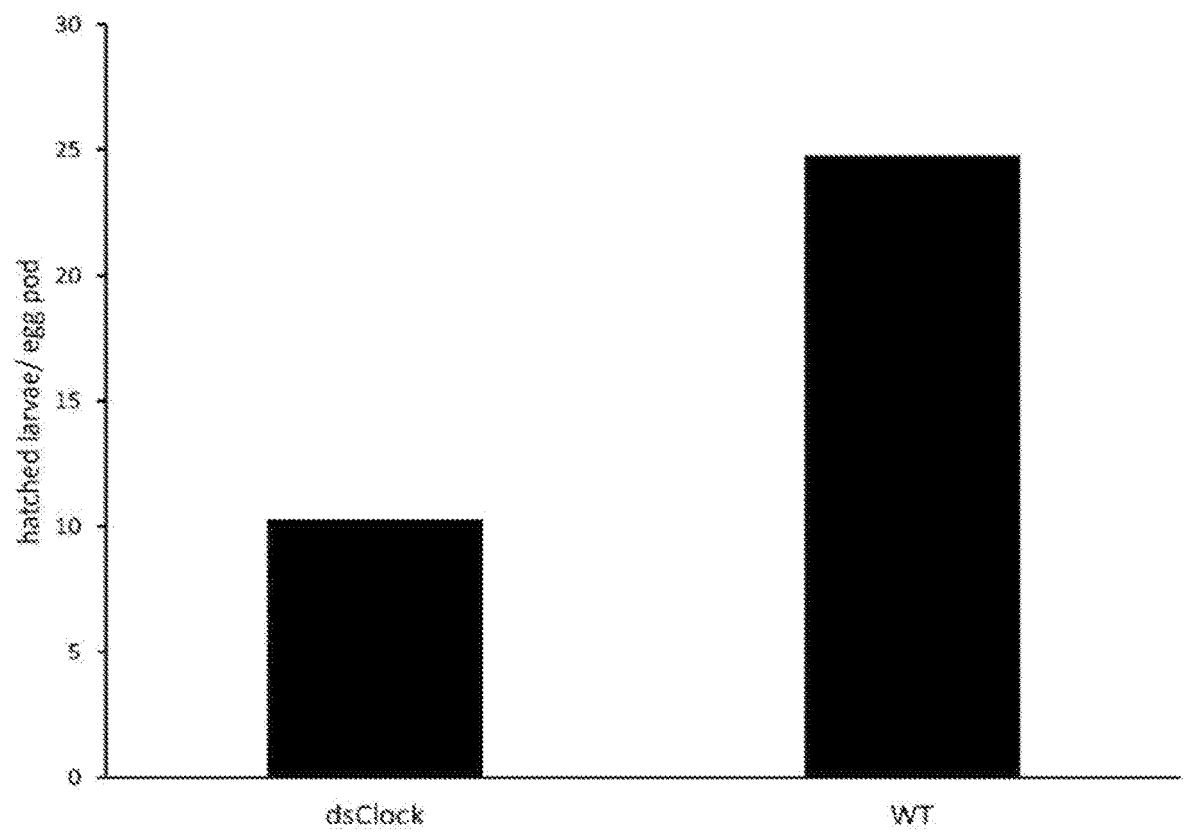
Figure 7B:
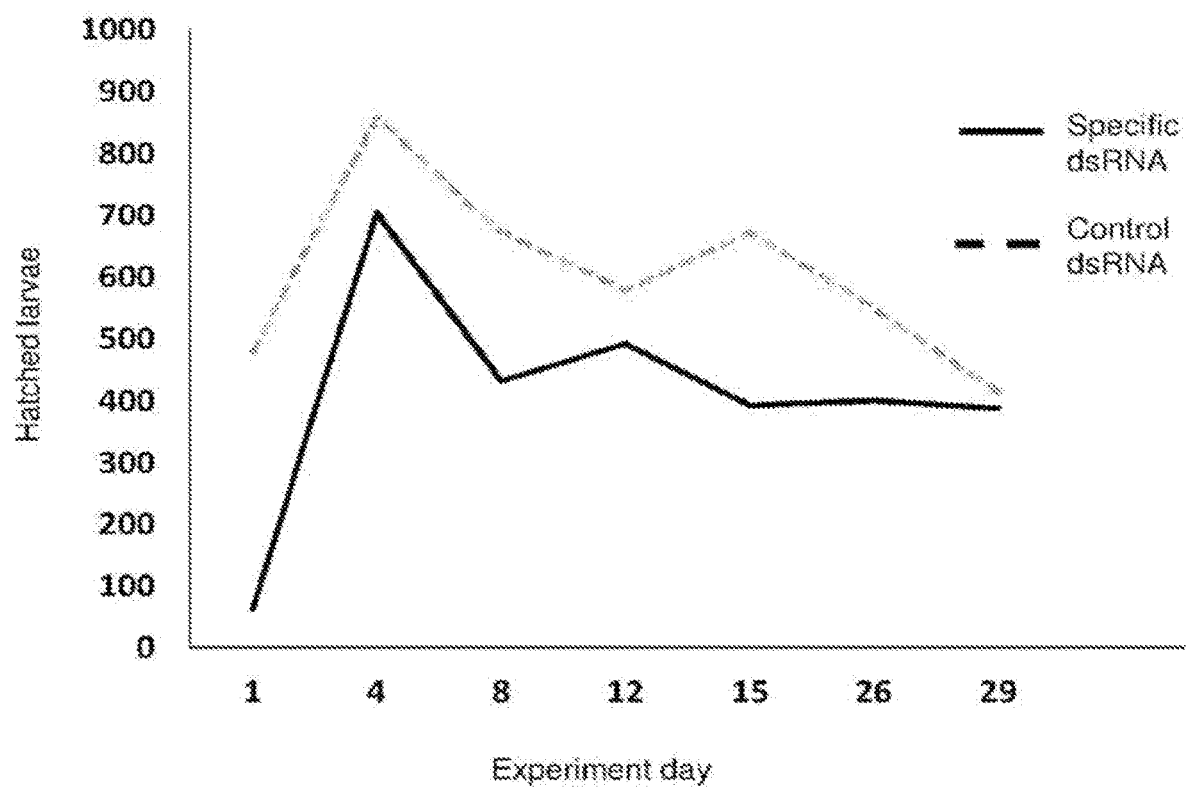

Example 3: Delivery by Feeding of an Intact dsRNA to *Spodoptera littoralis* Hemolymph Larvae of *Spodoptera littoralis* (*Prodenia littoralis*) at the 5$^{th}$ instar stage were placed in cultivation chambers, with 12 h/12 h light/dark illumination regime at constant temperature of 24° C. and relative humidity of 50%. Leaves of *Ricinus communis* (castorbean) were brushed with powder of transgenic algae expressing the dsRNA targeted to GFP (dsRNA-GFP) or of wild type algae such that all the leaves were homogenously covered with the algae powder (mixed with gelatin as described above). The *Spodoptera littoralis* were fed with the alga powder brushed leaves. For each treatment 5 independent repeats of 10 larvae each were used. Hemolymphs were collected from the fifth instar nymphs and were subjected to RNA preparation followed by qRT-PCR analysis using the specific primers of dsRNA-GFP (SEQ ID NOs. 9-10) and of TATA box binding protein (TBP) mRNA (SEQ ID NOs 7-8) as loading control (Table 4). The RT-PCR products were loaded on agarose gel. Full size amplicon products of 175 bp for the TBP segment were detected in all 8 hemolymphs samples (obtained from larvae fed with leaves covered with powder of wild type as well as of transgenic algae). Full size amplicon products of dsRNA-GFP of 83 bp were detected only in the 4 hemolymph samples of animals fed with dsRNA-GFP expressing algae and not in hemolymph of animals fed with WT algae (FIG. 5). These results further demonstrate the ability to deliver by feeding dsRNA molecules expressed in algae, in this example to larvae of *Spodoptera littoralis.*

Example 4: Reduced Expression of clk and Period mRNA Levels in Locusts by Feeding Nymphs with Algae Expressing dsRNA-Clock

*Schistocerca gregaria* timeless and period genes are two genes that their expression is directly regulated by clock protein. The expression level of these genes is often used to demonstrate downregulation of clock expression and activity (Tobback J et al., 2011, ibid).

Newly emerged *S. gregaria* fifth nymphs were placed at a density of 40 animals in 30×30×35 cm controlled chambers with 14 h/10 h light/dark illumination regime at constant temperature of 37° C. For each treatment 3 independent repeats of 40 locusts each were used. Wheat sprouts grown in pots were brushed with a powder of transgenic algae expressing either dsRNA targeted to clk (dsRNA-clock) or with a powder of wild type (WT) algae (algae powder mixed with gelatin as described above) till all the leaves were homogenously covered with the alga powder. The locusts were then fed with the algae-brushed wheat sprouts during 4 weeks. The wheat sprouts were brushed daily with the algae powder to ensure continuous treatment.

On days 8-11 and 28-30 of the experiment gonads and brains were harvested from young adults after the first molting, and from adult locusts, respectively, from each treatment. The organs were harvested 3 hrs after feeding. RNA was extracted and then subjected to reverse transcription followed by qRT-PCR analysis. The expressions of the locust's housekeeping genes GAPDH, (3-actin and of the clock and period genes were detected with specific primers. Relative quantifications of clock and period transcripts in locusts' gonads and brains were performed using the ΔCt method. The relative expression levels of the clock gene in locusts fed with leaves brushed with algae expressing dsRNA-clock was found to be down-regulated by 36% compared to locusts fed with leaves brushed with WT algae. The relative expression levels of the period gene in locusts fed with leaves brushed with algae expressing dsRNA-clock were found to be down-regulated by 27% compared to the locusts fed with leaves brushed with WT algae. GAPDH was used as a housekeeping gene (FIG. 6). The results demonstrate that algae can be used both as an expression and as an oral delivery tool to express dsRNA molecules which will downregulate specific genes in the target organism fed with the transgenic algae.

Example 5: Feeding Locust with Algae Expressing dsRNA Targeted to the Clock Gene Reduced the Locust Egg Fertility Instar larvae (stages 4-5) of the locust *Schistocerca gregaria* were continuously fed with wheat sprouts brushed either with powder of algae expressing dsRNA-clock or with WT algae as described above. On day 17, when the animals were sexually mature, pots filled with sand were placed in each cage to allow the females to lay eggs. The pots were collected every 48 hrs and incubated at 37° C. for 10 days to allow the larvae to hatch. The egg pods and the hatched larvae were counted and the ratio of hatched larvae to the number of the egg pods was calculated for each treatment. Locusts females fed with transgenic algae expressing the dsRNA-clock laid 31 egg pods among of which 128 were hatched, while locusts' female fed with WT algae laid 28 egg pods among of which 262 were hatched. The ratio of hatched larva to the number of egg pods (average of all repeats) was 2.3 fold lower in locusts fed with the dsRNA-clock expressing algae compared to locusts fed with WT algae (FIG. 7A).

In an additional experiment, *Schistocerca gregaria* third nymphs were placed at a density of 100 animals in 45×45×50 cm controlled chambers with a 14 h/10 h light/dark illumination regime at temperature range of 30-37° C. For each treatment 4 independent repeats of 100 locusts each were used. Wheat sprouts grown in pots were brushed with powder of transgenic algae expressing either dsRNA targeted to clk (dsRNA-clock) or dsGFP till all the leaves were homogenously covered with the alga powder. The locusts were then fed with the algae-brushed wheat sprouts during 4 weeks with daily new algae-brushed wheat sprouts to ensure continuous treatment. The animals were then counted and 10 male locusts and 10 female locusts (n=20) were placed in 45×45×50 cm controlled chambers with a 14 h/10 h light/dark illumination regime at temperature gradient of 30-37° C. in 4 independent repeats for each treatment. The animals were allowed to mate and lay eggs in plastic cylinders filled with sand for 36 days. Every 3 days the cylinders were replaced with fresh ones. The used cylinders were collected and placed in a controlled chamber with a 14 h/10 h light/dark illumination regime at temperature gradient of 30-42° C. Following 10-15 days of incubation hatched larvae were observed and counted. The number of larvae hatched from eggs of locusts fed with leaves brushed with algae expressing dsRNA-clock was lower compared to the number of larvae hatched from eggs of locusts fed with leaves brushed with dsGFP expressing algae throughout the experiment (FIG. 7B). Calculating the total number of larvae showed a 30% reduction in the number of larvae hatched from eggs of locusts fed with leaves brushed with dsRNA-clock expressing algae compared to the number of larvae hatched from eggs of locusts fed with control leaves (brushed with dsGFP expressing algae) (t-test=0.026) (FIG. 7A).

These results are in support with previous findings suggesting that the circadian clocks govern many metabolic and behavioral processes in an organism. In insects, these clocks and their molecular machinery have been found to influence reproduction in many different ways. Reproductive behavior including courtship, copulation and egg deposition, was found to be under strong influence of the daily rhythm (Tobback et. al 2011, ibid).

Figure 8A:
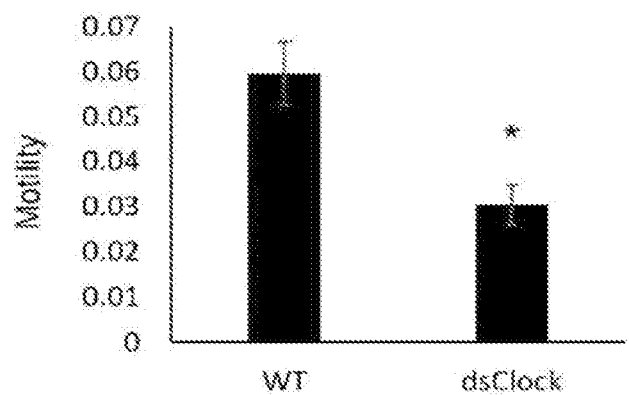
Figure 8B:
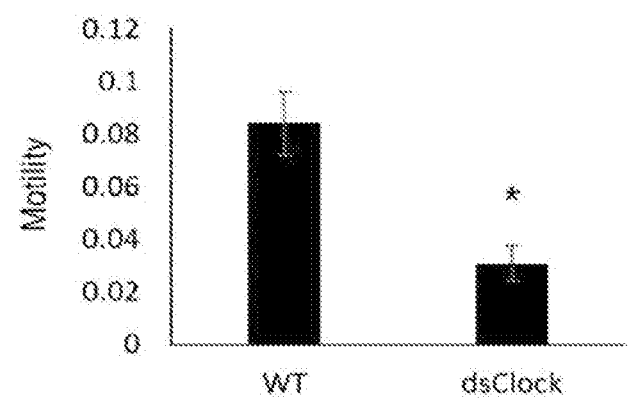
Figure 8C:
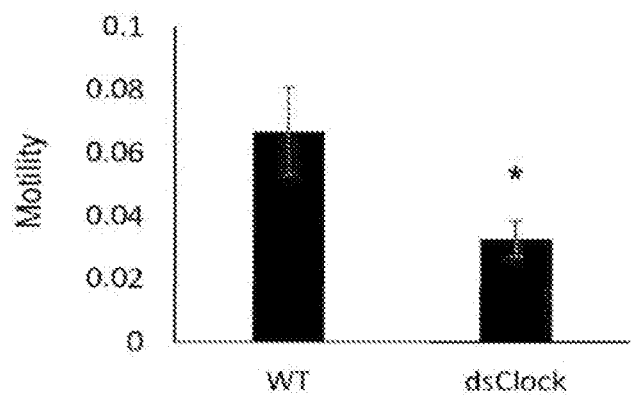

Example 6: Oral Delivery of Algae Expressing dsRNA Targeted Specifically Toward the clk Gene Reduced Locust Motility The locust Schistocerca gregaria were continuously fed with wheat sprouts brushed either with powder of algae expressing dsRNA-clock or with powder of WT algae (algae powder mixed with gelatin as described above). One cage from each treatment was continuously monitored with LifeCam HD-3000 camera and recorded with ActiveWebCam program. Measurements of the locusts' motility, during 3 days of feeding, demonstrated that the total motility of the locusts that were fed with the dsRNA-clock expressing algae was reduced by about 1.7-2.5 fold compared to the locusts that were fed with the WT algae (FIG. 8; A-C). Oral feeding of algae expressing dsRNA-clock reduced the locusts' activity compared to the control locusts which were fed with the WT algae.

Example 7: Delivery of an Intact dsRNA to Crustaceans by Feeding with Transgenic Algae Cherax quadricarinatus animals (30±10 g) were placed in cages dedicated to each treatment. The animals were fed daily for 28 days with feed pellet containing either dsRNA-GFP-expressing algae or with WT algae (7.5 gr algae/gr animal). On days 0 and 28, 72 hrs post feeding, 100 μl of hemolymph was sampled from each animal. For dsRNA-GFP-expressing algae 6 independent repeats were used and for WT algae 3 independents repeats were used. Hemolymphs collected were subjected to RNA preparation and the samples were analyzed by RNA dot blot hybridizations. The dot blot hybridization procedure was performed according to the manufacturer instructions (Roche Applied Science, cat #11 603 558 001, cat #11 585 762 001, cat #11 093 274 910, cat #11 685 627 001). Single-stranded RNA probes of dsRNA-GFP labeled with Digoxigenin-11-dUTP were synthesized from linearized template DNA according to the manufacturer's instructions (Roche Applied Science, Cat. No. 11175025910).

Figure 10:
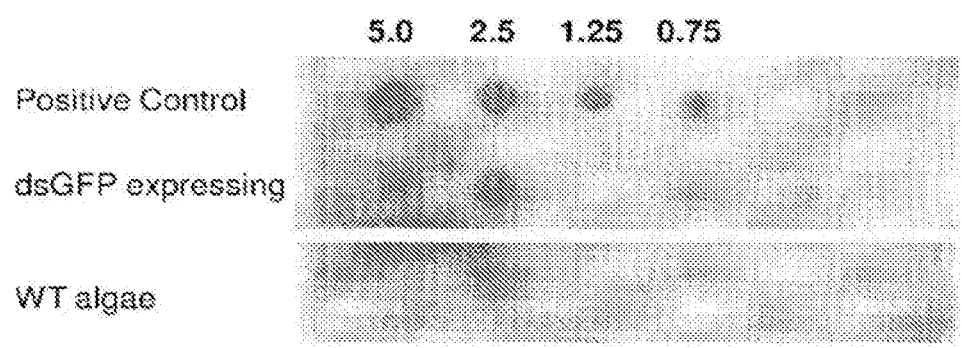

As is demonstrated in FIG. 10, positive signal of dsRNA-GFP was detected in four out of six hemolymph sample of the C. quadricarinatus which were fed with feed pellets comprising algae expressing the dsRNA-GFP, while no signal was detected in three out of the three hemolymph samples of C. quadricarinatus which were fed with feed pellets comprising the control algae. This result demonstrates for the first time that dsRNA molecules expressed in algae can be transferred to the hemolymph of crustaceans fed with the transgenic algae.

Figure 9:
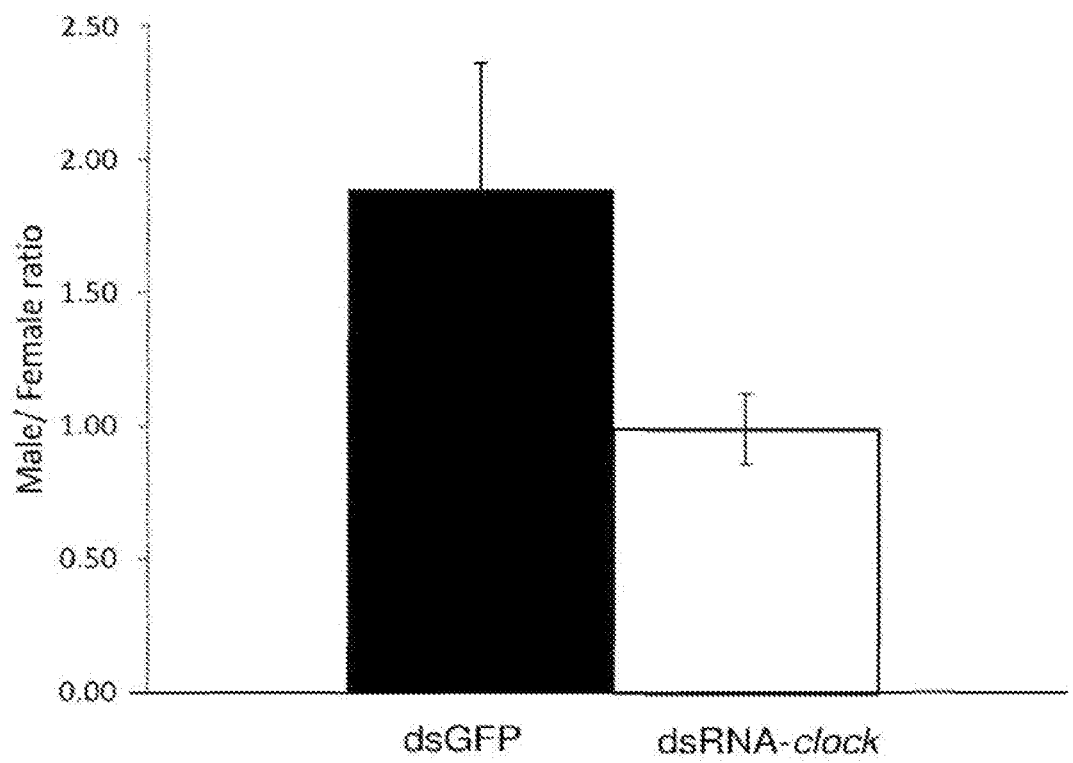

Example 8: Oral Delivery of Algae Expressing dsRNA Targeted Specifically Toward the Clk Gene Affects Male/Female Distribution in Schistocerca gregaria Schistocerca gregaria third nymphs were placed at a density of 100 animals in 45×45×50 cm controlled chambers with a 14 h/10 h light/dark illumination regime at temperature gradient of 30-37° C. For each treatment 4 independent repeats of 100 locusts each were used. Wheat sprouts grown in pots were brushed with powder of transgenic algae expressing either dsRNA targeted to clk (dsRNA-clock) or dsRNA targeted to GFP (dsGFP) till all the leaves were homogenously covered with the alga powder (algae powder mixed with gelatin as described above). The locusts were then fed with the algae-brushed wheat sprouts during 4 weeks with daily new algae-brushed wheat sprouts to ensure continuous treatment. Then the animals were counted and the ratio of males to females was calculated for each treatment. The ratio in locusts fed with leaves brushed with dsRNA-clock-expressing algae was significantly lower (p-value=0.01) compared to the locusts that were fed with leaves brushed with dsGFP expressing algae (48% reduction, FIG. 9). These results demonstrate that oral delivery of algae expressing dsRNA targeted to the clock gene in Schistocerca gregaria locusts resulted in an altered sex differentiation within the locust population. A linkage between the circadian clock and sexual development and behavior has been previously suggested. For example, the takeout gene was identified as a robust circadian-regulated gene. Dauwalder et. al suggested that the takeout gene family in Drosophila encodes multiple factors with sex-specific functions and proposed that it plays a role in integrating information about the organism's sex, nutritional status, and circadian cycle to affect adult male behavior (Dauwalder et. al. 2002. Genes & Development 16:2879-2892). The observed increase in the female number upon feeding S. gregaria with leaves covered with algae expressing dsRNA targeted to the clock gene suggest down regulation of the clock gene by the dsRNA.

Taken together, the present invention clearly demonstrates that feeding locust with transgenic algae expressing dsRNA targeted to a specific gene of the locust down regulate the expression and/or activity of the targeted gene.

Example 9: Freeze-Dried Algal Powder is not Viable

Algae liquid culture was harvested using the GEA Westfalia Separator (model SSD18-06-007, spin at 9790 rpm) or the Alfa Laval Separator model IFB 303X-73, at 7500 rpm. Algae paste was placed in either 1 cm×14 cm×14 cm trays or in 2 cm×25 cm×52 cm plates and stored at −80° C. for 24 hours. The next day the trays were freeze-dried using VirTis lyophilizer (item number 270389) at −50° C. and $2*10^{-1}$ Torr for 24-48 hours. Algal powder was used for a viability assay.

Figure 11A:
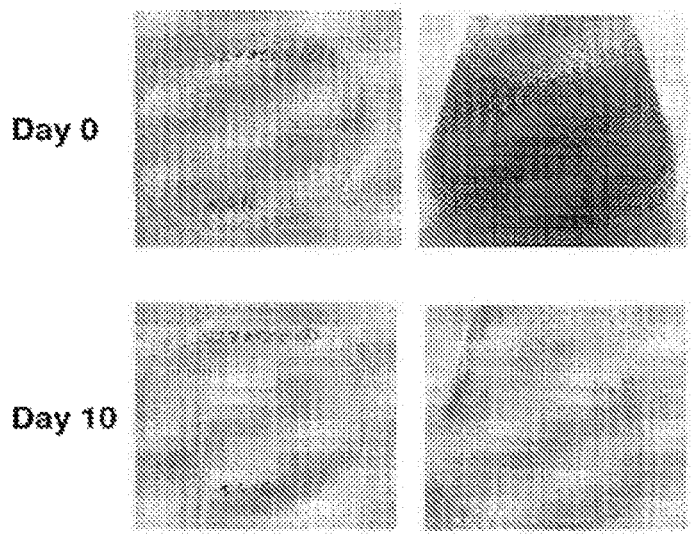
Figure 11B:
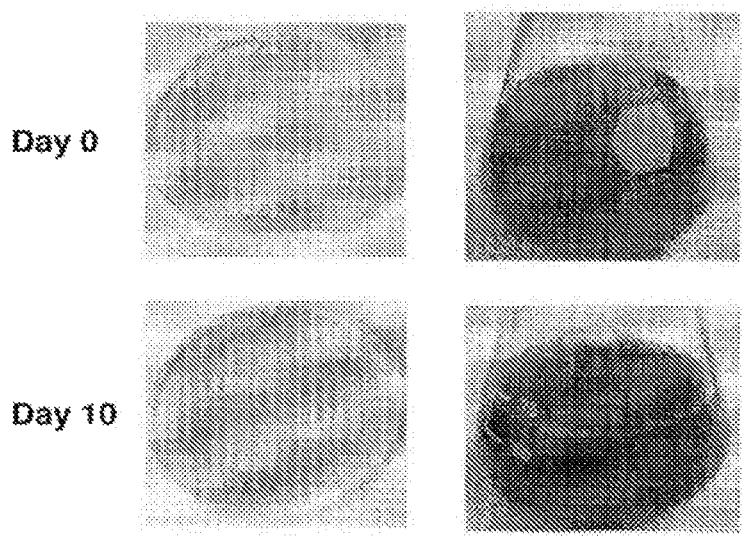

1 gram of freeze-dried *Phaeodactylum tricornutum* algae powder ($3.42*10^{10}$ cells) was mixed with 9 ml of ASW×1. 400 ul of the mixture were plated on either ASW agar plates or in suspension of ASW×1 and maintained for 10 days (FIG. 11A). Equivalent number of fresh *Phaeodactylum tricornutum* algae cells in liquid culture was plated under similar conditions. Cell growth was monitored after 10 days (FIG. 11B). No cell growth was detected in the freeze-dried algae powder cultures while the liquid algal culture grew nicely. The results demonstrate that the freeze drying procedures eliminates the viability of the algal cells.

Example 10: Construction of COPB2 dsRNA in Algae

The sense (SEQ ID NO:35) and antisense (SEQ ID NO:36) fragments of the *Lepeophtheirus salmonis* COPB2 gene are synthesized by Biomatik USA. The sense fragment is cloned by BamHI, SacII and the antisense fragment is cloned by EcoRI, KpnI. The fragments of COPB2 are cloned in the sense and antisense orientations into an intron contained pPhaT-cassette.

Example 11: Oral Delivery of Algae Expressing dsRNA Targeted Specifically Toward the COPB2 Gene Increases Mortality of *Lepeophtheirus salmonis*

Atlantic salmon (Salmo salary, with average body weight of 80 grams, are placed in plastic water tanks of 0.75 m³ and maintained in seawater (salinity 34.5 ppt) at a temperature of 10° C.). The fish are fed twice a day at 1% of their body weight with either commercial fish food homogenously coated with 15% of COPB2 dsRNA-expressing algal powder (w/w relative to total weight of fish food) or with commercial fish food that is homogenously coated with 15% (w/w) of algal powder expressing GFP dsRNA. For each treatment 3 independent repeats of 25 fish are used.

After 14 days of feeding the fish are challenged with 120 parasitic copepodids of the fish louse (*Lepeophtheirus salmonis*) for each water tank. 10 and 24 days after the additions of copepodids 5 fish of each group are anesthetized, sacrificed and the lice are counted under the microscope.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

---

The invention claimed is:

1. A non-propagating transgenic *Phaeodactylum tricornutum* microalga comprising at least one heterologous RNAi molecule, wherein the RNAi molecule is targeted to a clk gene present within an insect plant pest and wherein said RNAi molecule silences the expression of the clk gene present within the insect plant pest when the microalga is consumed by said insect plant pest, wherein said microalga is in a dried form.

2. The non-propagating transgenic *P. tricornutum* microalga of claim 1, wherein the RNAi molecule comprises a sense strand comprising at least 19 contiguous nucleic acids having at least 90% identity to the insect clk gene or a fragment thereof, and an antisense strand complementary thereto.

3. The non-propagating transgenic *P. tricornutum* microalga of claim 1 wherein said transgenic microalga is formulated in a form selected from the group consisting of an edible composition and a formulation to be applied onto a plant, wherein the edible composition or the formulation further comprises a substance selected from the group consisting of edible diluents, excipients, and carriers.

4. A method for inhibiting the expression of a clk gene within an insect plant pest, the method comprising providing to the insect plant pest an edible non-propagating transgenic *Phaeodactylum tricornutum* microalga comprising an RNAi molecule targeted to said clk gene present within said insect plant pest, wherein the microalga is in a dried form.

5. The method of claim 4, wherein the polynucleotide present within the organism is heterologous to said organism and wherein the RNAi molecule is targeted to a virus that infects the organism.

\* \* \* \* \*